United States Patent
Saxena et al.

(10) Patent No.: US 6,723,556 B1
(45) Date of Patent: Apr. 20, 2004

(54) NUCLEIC ACID ENCODING A FRAGMENT OF BOVINE LUTEINIZING HORMONE/CHORIONIC GONADOTROPIN RECEPTOR

(75) Inventors: Brij B. Saxena, Englewood, NJ (US); Premila Rathnam, Englewood Cliffs, NJ (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 08/120,324

(22) Filed: Sep. 14, 1993

Related U.S. Application Data

(63) Continuation of application No. 08/029,613, filed on Mar. 11, 1993, now abandoned, which is a continuation-in-part of application No. 07/879,245, filed on May 6, 1992, now abandoned, which is a continuation-in-part of application No. 07/742,236, filed on Aug. 8, 1991, now abandoned, which is a division of application No. 07/555,696, filed on Jul. 23, 1990, now abandoned, which is a division of application No. 06/910,554, filed on Sep. 23, 1986, now Pat. No. 4,966,888, which is a continuation-in-part of application No. 06/752,497, filed on Jul. 8, 1985, now abandoned, which is a continuation of application No. 06/446,145, filed on Dec. 2, 1982, now abandoned.

(51) Int. Cl.[7] .............................................. C12N 15/12
(52) U.S. Cl. .................. 435/320.1; 435/69.1; 536/23.5
(58) Field of Search .................. 536/23.5; 435/69.1, 435/69.7, 172.1, 361, 320.1; 530/351, 395; 935/9

(56) References Cited

U.S. PATENT DOCUMENTS

| 5,208,144 A | * | 5/1993 | Smith et al. |
| 5,565,335 A | * | 10/1996 | Capon et al. |
| 5,800,996 A | * | 9/1998 | Lee et al. |
| 5,948,614 A | * | 9/1999 | Chatterjee |
| 5,955,363 A | * | 9/1999 | Lewis et al. |

FOREIGN PATENT DOCUMENTS

| EP | 0 332 581 | * | 3/1989 |

OTHER PUBLICATIONS

K.C. McFarland et al., Science 245:494–499, Aug. 4, 1989.*
H. Loosfelt et al., Science 245:525–528, Aug. 4, 1989.*
A.L. Frazier et al., Mol. Endocrinology 4:1264–1273 (1990).*
T. Minegish et al., Biochem. Biophys. Res. Comm. 172:1049–1054 (1990).*

* cited by examiner

*Primary Examiner*—Lorraine Spector
(74) *Attorney, Agent, or Firm*—Sughrue Mion, PLLC

(57) ABSTRACT

Purified hCG-hLH receptor, hCG-hLH receptor-hCG complex and combinations between their subunits as antigens, as well as antibodies thereto which are useful as a contraceptive vaccine. Antibodies to LH-R are useful in regulating steroid hormone production. Nucleic acid sequences encoding polypeptides with LH receptor activity were obtained and sequenced.

2 Claims, 6 Drawing Sheets

NUCLEIC ACID ENCODING A FRAGMENT OF BOVINE LUTEINIZING HORMONE/CHORIONIC GONADOTROPIN RECEPTOR

CROSS-REFERENCE TO RELATED APPLICATIONS

This is a Continuation of application Ser. No. 08/029,613 filed Mar. 11, 1993 now abandoned which is a continuation-in-part of Ser. No. 07/879,245, filed May 6, 1992, now abandoned, which is a continuation-in-part-of Ser. No. 07/742,236, filed Aug. 8, 1991, now abandoned, which is a divisional of 07/555,696, filed Jul. 23, 1990, now abandoned, which is a divisional of 06/910,554, filed Sep. 23, 1986, which matured into U.S. Pat. No. 4,966,888, which is a continuation-in-part of Ser. No. 06/752,497, filed Jul. 8, 1985, now abandoned, which is a continuation of Ser. No. 06/446,145, filed Dec. 2, 1982, now abandoned. All of the applications noted hereinabove are hereby incorporated by reference.

The invention herein was made in the course of work under one or more grants from the United States Department of Health and Human Resources.

FIELD OF THE INVENTION

The present invention relates to purified hCG-hLH receptor, hCG-hLH receptor-hCG complex and combinations between their subunits as antigens, as well as antibodies thereto which are useful as a contraceptive vaccine and nucleotide sequences encoding polypeptides with receptor activity.

BACKGROUND OF THE INVENTION

In recent years significant effort has been expended toward developing an immunological approach to contraception. The basic approach has been to either provide an antibody (passive immunization), or to elicit an antibody response (active immunization), to a hormone critical to the establishment and/or maintenance of pregnancy. The production and effects of human chorionic gonadotropin (hCG) in pregnancy have singled out hCG as a prime candidate for studies in immunological contraception. hCG is not present in the normal, healthy female prior to fertilization, but is secreted by the developing blastocyst and can be detected in pregnant women as early as 6 to 7 days after fertilization. hCG, in turn, initially acts upon the corpus luteum, and later upon the placenta, in causing each of them to secrete progesterone. Progesterone, at a high level, acts upon the endometrium to aid in preparing it for implantation and to maintain it after implantation. Therefore, both hCG and progesterone are essential for pregnancy to proceed immediately following fertilization. However, a significant reduction of hCG level prevents sufficient hCG from interacting with the hCG receptors of the corpus luteum and the placenta for maintenance of the high level of progesterone required for pregnancy. Progesterone drops back to or remains at a level too low for support of the endometrium, in the absence of hCG.

A number of researchers have attempted to develop contraceptive vaccines which immunologically block progesterone production. These vaccines provide or produce hCG antibodies to immunologically interact with circulating hCG determinants, thereby preventing the hCG determinants from reaching the hCG receptors of the corpus luteum and of the placenta.

Various problems have prevented commercialization of an hCG vaccine. First, hCG is a human hormone and humans will not normally produce antibody to a human hormone. This problem has been attacked by linking the hCG to a protein such as a hapten. Of course, the hCG antibodies can be produced in normal fashion in animals such as rabbits. However, problems still occur due to the non-specificity of hCG antibody, i.e., high levels of hCG antibody cross react with human luteinizing hormone (hLH); high levels of hCG antibody tend to cause abortion; etc. Low levels of hCG antibodies, which would not cross react with hLH, i.e., are hCG-β specific, were thought to offer the best chance of success, but in practice the circulating life of hCG is extended by formation of loose antigen-antibody complexes.

hCG and hLH, which share common receptors in the gonads as well as follicle stimulatory hormone (FSH), play important roles in the growth of ovarian follicles and in spermatogenesis in the testes.

A group of patents by Bahl (U.S. Pat. No. 4,310,455 and others) concern modification of the β subunit of hCG to produce a more specific hCG antigen for a variety of uses, including a contraceptive vaccine.

U.S. Pat. No. 4,161,519 by Talwar discloses a contraceptive vaccine comprising a purified β subunit of hCG conjugated to an antigen carrier.

A number of papers related to the general subject of contraception based on tying-up circulating hCG are found in *Recent Advances in Reproduction and Regulation of Fertility*, Elsevier/North Holland, 1977 (G. P. Talwar, Editor), pages 427–485.

Luborsky & Behrman (Biochem. Biophys. Res. Comm. 90, 1407, 1979) used rat ovary detergent lysates as a source of LH-R. Polyclonal antibodies thereto reacted with rat gonadal tissues but not with human or sheep ovary. The antiserum blocked LH-induced progesterone secretion by rat luteal cells.

Metsikko & Rajaniemi (Endocrinology 109, 1399, 1981; Biochem. J. 224, 467, 1984) prepared an antiserum to purified LH receptor from rat ovarian tissue. The receptor was presaturated with hCG prior to use as immunogen. The resulting antiserum immunoprecipitated a polypeptide of about 95,000 molecular weight. Those findings are at odds with that reported in the instant invention.

Podesta et al. (Proc. Natl. Acad. Sci. 80, 3986, 1983) described a monoclonal antibody raised to a rat ovarian membrane preparation. The antibodies inhibited testosterone production by isolated Leydig cells exposed to LH.

Rosemblit et al. (Endocrinology 123, 2284, 1988) described a polyclonal antiserum raised to purified rat LH receptor. The receptor had a molecular weight of about 93,000 daltons. Rosemblit et al. distinguished their antibody over that of Metsikko & Rajaniemi and of Podesta et al.

Vuhai-Luuthi et al. (Endocrinology 127, 2090, 1990) described monoclonal antibodies directed to porcine LH receptor complexed with human chorionic gonadotrophin. The antibody immunoprecipitated a major protein of 85,000 molecular weight, and two minor proteins of approximately 68,000 molecular weight and about 45,000 molecular weight. The 85,000 molecular weight protein was found in both testicular membrane extracts and ovarian membrane extracts.

SUMMARY OF THE INVENTION

Therefore, it is an object of the present invention to provide an improved contraceptive vaccine.

A more specific object of this invention is to provide a contraceptive vaccine which functions by preventing hCG from stimulating progesterone production of the corpus luteum and/or placenta.

Still another object of the present invention is to provide a contraceptive vaccine which overcomes the problems encountered with only hCG-based vaccines of the prior art.

A further object of the present invention is to provide contraceptive vaccines which can be used for either passive or active immunization.

Another object of the invention is to provide antibodies to LH-R which can modulate sex hormone secretion.

Yet another object of the instant invention is to provide nucleotide sequences that encode polypeptides capable of binding hCG and hLH and bindable by α-receptor antibodies.

Since hCG and hLH have common receptors an additional object of the present prevention is to use hCG-hLH receptor as an antigen and antibodies thereto in order to reversibly retard ovarian follicular growth and corpus luteum function which is believed to prevent ovulation and thus fertility.

Other objects of the invention, such as the provision of novel antigens and antibodies and methods to obtain such, will be apparent to the skilled artisan from the Detailed Description of the Invention, hereinbelow.

In accordance with the present invention, there is provided a contraceptive vaccine based on hCG, or a derivative; fragment or subunit thereof, and the common receptor for hLH and hCG, or a derivative, fragment or subunit thereof. In preferred embodiments of the invention, a dual purpose antigen is formed by complexing or conjugating the hCG-β subunit, or a derivative or fragment thereof, to the common biological receptor for hCG and hLH, or a derivative, fragment or subunit thereof. In active immunization embodiments, the two antigen components used in the present invention are administered either separately or in the form of the above-described complex or conjugate. In passive immunization embodiments, the antigen materials, separately or as the conjugate, are administered to a lower animal for production of antibodies, which are collected in the usual fashion and administered as a vaccine. In the most preferred embodiments of the present invention, only the common receptor for hLH and hCG, or a derivative, fragment or subunit thereof, is employed for either active or passive immunization as well as for the production of monoclonal antibodies for use as contraceptive agents.

As noted above, in the preferred embodiments of the invention, hCG-β is linked or complexed with the biological receptor for hCG and hLH (hereinafter "receptor") to form an antigen hCG-receptor unit capable of circulation in the bloodstream as an integral moiety. As disclosed herein, either the antigen hCG-receptor unit can be administered as a contraceptive vaccine as in the preferred embodiment of the invention or the antigen receptor only can be administered as a contraceptive vaccine as in the most preferred embodiment of the present invention, or in another embodiment at this time, antibody to either the hCG-receptor antigen or the receptor antigen can be administered as the contraceptive vaccine.

The common receptor for hLH and hCG is antigenic, so that the antibodies produced in response to the hCG-receptor unit contain determinants for both hCG and the receptor. In this manner, some of the antibodies of this invention not only interact with hCG to prevent hCG from reaching the receptors of the corpus luteum and placenta, but also blocks the receptor sites, thereby preventing any remaining unbound hCG from reaching the receptor sites.

In preferred embodiments of the invention, the hCG antigen consists essentially of the hCG-β subunit, or a derivative or fragment thereof, intact or modified.

In other preferred embodiments of the invention, the antibodies of the invention contain essentially monospecific determinants for the hCG-β subunit and essentially monospecific determinants for the receptor.

In passive immunization of the present invention, bifunctional and/or mono-functional polyclonal or monoclonal antibodies may be involved as well as idiotypic antibodies.

DETAILED DESCRIPTION OF THE INVENTION

Figure 1:
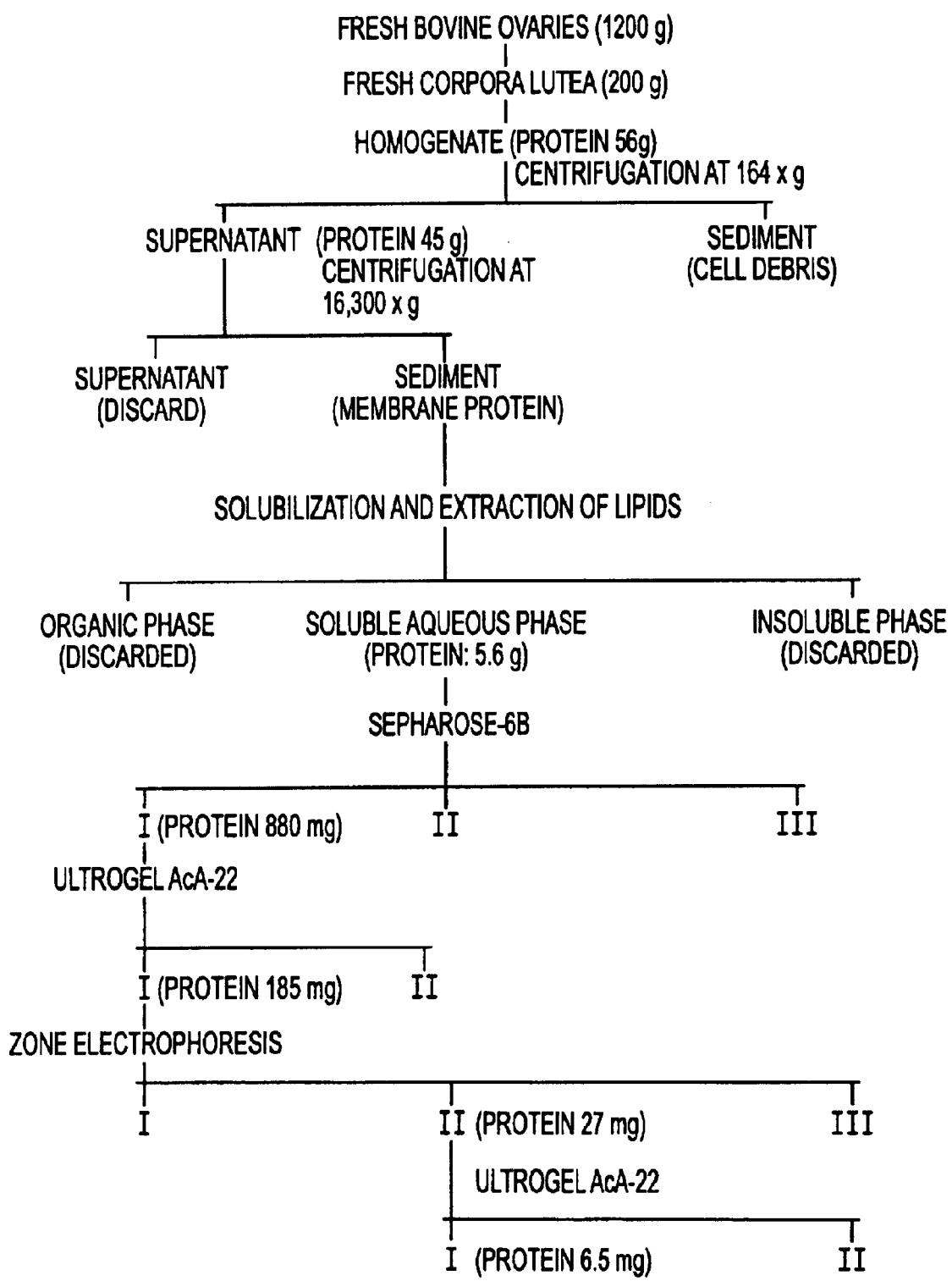
FIG. 1 is a flow diagram of the most preferred receptor purification method of the present invention which is described in Reference Example 2.

The concept underlying the present invention is the provision of antibodies (1) capable of blocking the determinant(s) of hCG which interact with the sites of the biological receptor for hCG, and/or (2) capable of interacting with said receptor sites. Therefore, (1) the determinants of hCG normally available for interaction with receptor sites are tied-up by antibody and/or (2) the sites of the receptor normally available for receiving hCG are blocked by antibody being associated therewith. The dual function of some of the antibodies used herein should provide effective contraception with relatively low antibody titers which is a key concept of this invention.

Although it is possible to utilize two separate antigens in the preferred embodiment of this invention, namely hCG (preferably hCG-β) and receptor, it is preferred to use a bifunctional antigen formed by linking or associating hCG with its receptor. Thus, one key reagent of the present invention is the common receptor for hLH and hCG.

The present inventors have previously isolated essentially pure receptor from naturally-occurring sources. Much of this work is described in application Ser. No. 311,736, filed 15 Oct. 1981, now abandoned, and the continuation-in-part application thereof, application Ser. No. 440,477, filed 9 Nov. 1982, now U.S. Pat. No. 4,560,649, both of which are incorporated herein by reference in their entirety.

It is preferred to use as the receptor antigen component herein, a relatively pure receptor fraction or subunit thereof, such as the electrophoretically homogeneous receptor and/or subunits thereof described in said U.S. Pat. No. 4,560,649. It is most preferable to use as the receptor antigen component herein, a relatively pure receptor fraction or a subunit thereof obtained as described in Reference Example 2 below. However, less pure receptor fractions, such as those disclosed in Saxena patents U.S. Pat. No. 4,016,250 and U.S. Pat. No 4,094,963 and/or obtained from steps prior to the electrophoresis step of the purification processes of said co-pending Saxena et al. applications, could be considered for use, but it is expected that superior results will be obtained with the purified receptor fractions. A substantially pure receptor fraction is preferred to reduce production of non-specific antibody.

The present inventors anticipate future modified forms of the receptor once additional analytical work is carried out on their electrophoretic homogeneous fraction, such as amino acid sequencing and analysis of the receptor and/or its oligomeric forms. Naturally, such a modified product of the receptor will be very useful in the practice of the present invention. Hereinbelow, there are set forth procedures for obtaining a purified receptor product and characterization of the electrophoretically pure receptor fraction.

As used herein, receptor activity indicates a polypeptide either with capacity to bind hCG/hLH or that is recognized by α-LH receptor antibody.

The antibodies of the instant invention are useful in obtaining nucleotide sequences that encode polypeptides with LH receptor activity. As noted herein, various molecular weight species of polypeptides have LH receptor activity. The nucleotide sequences are useful in assessing the structure-function relationships of the various species of polypeptides and of the holoreceptor.

REFERENCE EXAMPLE 1

Receptor Purification 1,200 bovine ovaries stored at −60° C. were thawed. The corpora lutea therefrom were homogenized for 15 to 20 seconds in 0.1 M Tris-HCl buffer (pH 7.4, containing 1 mM each of $CaCl_2$, $MgCl_2$ and dithiothreitol, 0.01% sodium azide, $10^{-6}$M phenymethylsulfonyl fluoride) and 100 $\mu$/ml soy bean trypsin inhibitor containing 15% sucrose in a tissue to buffer ratio of 1:10 (w/v). The homogenate was centrifuged for 30 minutes in 8 one liter capacity swing-out buckets at 1,000 rpm (Sorvall, Newton, Conn.). The supernatant was recentrifuged at 7,000×g for 45 minutes. The yield was 100 grams of protein. The 7,000×g supernatant was concentrated 8-fold by an Amicon DC-10 unit equipped with Hl-50 hollow fiber cartridge (Amicon, Lexington, Mass.) suspended in an equal volume of the Tris-HCl buffer, reconcentrated to the original volume to reduce sucrose concentration and stored in 200 ml aliquots at −60° C. (All temperature values herein are centigrade unless stated otherwise.) The yield at this stage was 77 grams of protein. This concentrate can be diluted with buffer and reconcentrated.

Next, the above obtained concentrated supernatant was fractionated by a linear sucrose density gradient centrifugation. This was accomplished by preparative fractionation of aliquots of 200 ml each (20 g protein) of the concentrated 7,000×g supernatant in a Beckman Model L2-65B refrigerated ultracentrifuge, using a 1.6 liter capacity rotor (Ti-50). A linear sucrose gradient from 35% to 10% was prepared by the aid of a Beckman gradient pump (Model No. 141). The sample was layered on top of the sucrose gradient, the rotor was accelerated to 30,000 rpm and the centrifugation was continued for two hours. The rotor was then decelerated to maintain 3,500 rpm. The sucrose density gradient was eluted by displacement with a 40% sucrose solution and 20 ml fractions were collected every 0.5 minute. Fractions were analyzed for specific binding by $^{125}$I-hCG. Two fractions eluted between 18 to 28% sucrose contained nearly all of the active receptor. Sucrose concentration was measured by refractive index. The obtained fractions totaled 6.2 g protein.

Thereafter, the two fractions were separately concentrated by an Amicon DC-2 unit equipped with a HI-50 cartridge. Then, the samples were diluted with the Tris-HCl buffer and re-concentrated in the same apparatus. Finally, this phase of the purification process was completed by centrifuging at 55,000 rpm for 4 hours to sediment the receptor protein. Percent recoveries for the two fractions were 60% and 92%, respectively. The sediments are combined at this point. The 10 mM Tris-HCl buffer (pH 7.2, containing 0.5% Triton X-100) was added to the receptor fraction (25 mg protein per ml). 1% Triton X-100 solubilized more protein but significantly reduced hormone binding activity, perhaps due to formation of Triton X-100 micelles. The suspension was sonicated at 50 watts, four times for 5 second duration each time at 4° C. to increase receptor protein solubilization and recovery of hormone-binding activity. The neutral lipids were extracted by shaking with an equal volume of chilled petroleum ether at 4° C. for one hour and finally centrifuging at 10,000 rpm for one hour. The organic solvent, the aqueous phase, and the insoluble residue were separated. The aqueous phase contained the solubilized receptor.

The aqueous layer was recentrifuged at 5,000 rpm and 943 mg of protein recovered. This product was purified by gel filtration on a column of Sepharose-6B. The column was eluted with the Tris-HCl buffer (pH 7.2, containing 0.5% Triton X-100) at a flow rate of 13.5 ml per hour. Six ml fractions were collected and tested for receptor using $^{125}$I-hCG, the fractions having significant receptor activity were pooled and then fractionated on multiple 2.8×35 cm columns of Sepharose-4B. It was found that the ascending chromatography on Sepharose-6B separated a large amount of the adenylate cyclase activity (retarded protein fraction) from the hormone binding activity (unretarded protein fraction). The sample at this point contained 22 mg protein per 15 ml of the Tris-HCl buffer. Column elution was carried out using the Tris-HCl buffer (pH 7.2, containing 0.5% Triton X-100) at a flow rate of 8 ml per hour. 4 ml fractions were collected. In essence, the fraction obtained from the Sepharose-6B column was sub-divided into two fractions by the Sepharose-4B columns, one fraction containing most of the hormone binding activity (unretarded protein fraction) and the other fraction containing most of the 5'-nucleotidase activity (retarded fraction). Again, through testing by specific binding to $^{125}$I-hCG, the active fractions were pooled. The active fractions from four Sepharose-4B columns were concentrated 5-fold by an Amicon ultrafilter and gel-filtered through a 5×50 cm column of Ultrogel AcA-34 (LKB Instruments).

The Ultrogel AcA-34 column was eluted with 0.3 M lithium borate buffer (pH 7.2, containing 1 mM $MgCl_2$, 0.01% $NaN_3$ and 0.5% Triton) at a flow rate of 10 ml/hour. 4 ml fractions were collected. The Ultrogel AcA-34 significantly reduced the Triton X-100 concentration to about 0.5%.

At this point, the sample consisted of 73.5 mg of protein in the lithium-borate buffer. Vertical zone electrophoresis was carried out on a 3×42 cm column of cellulose. The cellulose powder was equilibrated in the lithium borate buffer, decanted and then packed into the column. The column was washed extensively with the same buffer prior to electrophoresis. The receptor protein was equilibrated in the same buffer by dialysis. The conditions of electrophoresis were 60–80 mA, 300–315 volts, 72 hours duration. The column was eluted with the lithium borate buffer. Fractions containing the receptor were concentrated by ultrafiltration and chromatographed on Ultrogel AcA34 columns in the lithium borate buffer to remove excess Triton and to concentrate into a smaller volume. At this stage, the purified produce weighted 6.52 mg. The binding capacity of the original 7,000×g supernatant, the first Ultrogel fraction and the product at this stage were approximately 5.15, 310 and 2,681 pM hCG/mg protein (affinity constant (Kd) of 0.76× $10^{-10}$ liter $M^{-1}$), respectively, which represents approximately an 11,805-fold purification of the protein in the 7,000×g supernatant and a final 536-fold increase in receptor binding capacity.

A further purification step was carried out by immune-affinity column chromatography on hCG bound anti-hCG Sepharose-4B matrix. The receptor specific activity as compared to the zone electrophoresis product increased only by 1.05 fold.

The molecular weight of the aggregate of the electrophoretically pure receptor glycoprotein was found to be about 5.9 million using gel permeation chromatography, as described more fully hereinafter. Purification has advanced to the degree that analysis of the receptor material by disc-gel electrophoresis following treatment hereinafter disclosed yielded a single glycoprotein-band, of about 280 thousand molecular weight. (All molecular weights, amino acid analyses and carbohydrate analyses of the receptor protein and components thereof disclosed herein are understood to be within the normally accepted error of 10% of the value disclosed.) Various protein markers were used to estimate the aggregate molecular weight as well as the molecular weights of the various aggregate oligomers and subunits disclosed hereinafter. Accordingly, one embodiment of this invention involves the use of an electrophoretically homogeneous hLH-hCG receptor glycoprotein of about 5.9 million molecular weight composed of a plurality of glycopolypeptide components, probably linked to one another through disulfide bonds to form said glycoprotein aggregate, said glycoprotein aggregate component appearing as a single entity as determined by disc-gel electrophoresis.

Although it is believed that the isolated receptor could be obtained from the corpus luteum of various species of animals having the common receptor for hLH and hCG, as well as from other receptor sources such as those disclosed hereinbefore (and also could be synthetically produced following further structural analyses such as amino acid sequence) the present inventors obtain it from bovine corpora lutea. Thus, a more specific embodiment of the receptor for use herein involves a detergent solubilizable, electrophoretically pure, hCG-hLH receptor glycoprotein of bovine corpora lutea, as above defined, and having a specific binding capacity of at least 2,000 pM hCG/mg protein, preferably at least 2,500 pM hCG/mg protein.

Binding capacity was performed in albumin by equilibration of the protein sample with approximately 50,000 cpm equivalent to 1.25 ng of $^{125}$I-hCG, in the presence of increasing concentrations of unlabeled hCG from 0.25 to 20,000 ng. Conventional incubation procedures were used, with the addition of an equal volume of 15% (w/v) polyethylene glycol 6,000, dissolved in phosphate buffered saline, to the incubate to precipitate the hormone-receptor complex. Thereafter, the tubes were shaken, centrifuged and the supernatant aspirated. Sediments were resuspended in buffer, again mixed with the polyethylene glycol and recentrifuged. Radioactivity of the pellet, representing 125I-hCG receptor complex was determined. Specific binding and affinity constants were calculated according to the method of Scatchard, G., Ann., N.Y. Acad. Sci., 51:660 (1949).

Disc-gel electrophoresis was carried out using sodium dodecyl sulfate (hereinafter "SDS")-polyacrylamide gel disc electrophoresis as follows:

The purified hLH-hCG receptor fraction was analyzed by SDS-polyacrylamide disc-gel electrophoresis, according to the method of King and Laemmli, J. Mol. Biol., 62:465 (1971) with minor modifications, to yield an optimum resolution of protein components. Aliquots of 30–60 µg of purified fractions of the hLH-hCG receptor were solubilized in 0.5% Triton X-100, lyophilized and dissolved in 100 41 µl water. Samples were then dialyzed for 48 hours against 0.125 M Tris-HCl buffer (pH 8.0, containing 1 mM EDTA). Samples were heated in boiling water in the presence of 2% SDS alone or 2% SDS and 1% mercaptoethanol (M.E.), for 1½ minutes. Protein markers of known molecular weights dissolved in Tris-HCl buffer and treated with 2% SDS and 1% M.E. were applied on the stacking gel and electrophoresed simultaneously. The electrophoreses were performed in 0.025 M Tris-glycine buffer (pH 8.3, containing 0.1% SDS). After the electrophoreses, the gels were removed from the glass columns and the protein bands were stained with Coomassie Blue. The relative mobilities ($R_f$) of the protein markers and of the purified receptor fractions were calculated, and a relationship was established between the $R_f$ and logarithm of molecular weight of each marker protein, to calculate the molecular weights, of the purified receptor samples. The 5.9 million aggregate sample treated with 2% SDS yielded a single glycoprotein band of approximately 280,000 molecular weight. The sample treated with SDS plus M.E. yielded three bands of approximately 160,000; 57,000 and 44,000 molecular weights, suggesting the presence of oligomers, probably disulfide linked.

Prior to disc-gel electrophoresis, the receptor protein obtained after cellulose zone electrophoresis was subjected to gel permeation chromatography on a column of Sepharose-4B to determine molecular weight. After gel filtration, the unretarded fraction of receptor protein is the 5.9 million molecular aggregate, as above disclosed. The column was eluted with 10 mM Tris-HCl buffer (pH 7.2, containing 1 mM MgCl$_2$, 0.0170 NaN$_3$ and 0.5% Triton X-100).

Further experimentation was carried out to determine the components or units forming the 5.9 million aggregate. In each case, the molecular weight estimate was determined using gel permeation chromatography as described below.

Attempts were made to deaggregate the 5.9 million molecular weight protein into its largest polypeptide units.

Gel permeation chromatography of the receptor glycoprotein was carried out before and after the various treatments described below. (A protein concentration of approximately 1 mg/ml was used for each treatment.) In each case, the gel columns were equilibrated and eluted with appropriate solvents containing 0.5% Triton X-100. Standards of known molecular weight (DNA (supercoiled) blue dextran, thyroglobulin, ferritin, aldolase and catalase) were gel-filtered through the columns and gels selected to resolve the approximate range of the molecular sizes of a protein marker. The $K^{av}$ (index of solute migration in gel chromatography) for each marker and for each receptor component was calculated from its elution volume. The molecular weights of the receptor components were determined from a standard curve of $K_{av}$ versus the molecular weights of the known protein markers.

Treatment with 1 M NaCl overnight at 4° as well as with 2% SDS and 1% mercaptoethanol at 4° did not alter the molecular weight of the receptor protein aggregate. However, treatment with 2% SDS, at 100° for 1½ minutes, deaggregated the 5.9 million molecular weight material into a plurality of a 280,000 molecular weight species, which was separated on a Sepharose-6B column, of the hormone-free hLH-hCG receptor. The Sepharose-6B column was eluted with 0.1 M acetic acid containing 1 mM MgCl$_2$, 0.01% NaN$_3$, 0.1% SDS and 0.5% Triton X-100. When the 280,000 molecular weight species was incubated with $^{125}$I-hCG, and, applied to a Sepharose-6B column, a major hormone-bound component with a molecular weight of 185,000 was recovered by elution with 10 mM Tris-HCl buffer (pH 7.2, containing 1 mM $MgCl_2$, 0.01% $NaN_3$ and 0.5% Triton X-100). If a molecular weight of 40,000 is subtracted for hCG from the 185,000 molecular weight species, the resulting molecular weight of 145,000 suggests the presence of a dimer of the receptor of approximately 280,000 molecular weight. That is, the 280,000 species dissociates into two oligomers of approximately 145,000 molecular weight each. Both the binding of $^{125}$I-hCG or covalent linking of $^{125}$I-hCG alone cause the reduction of the 280,000 molecular weight dimer, and the appearance of the hormone-bound 185,000 molecular weight forms of the receptor.

In another set of experiments, the 280,000 molecular weight component following treatment for 1½ minutes at 100° with 2% SDS and 1.5 mM DTT (dithiothreitol) followed by gel filtration on a column of Ultrogel AcA-34, yielded a 120,000 molecular weight species of the hLH-hCG receptor by elution with a 0.01 M Tris-HCl buffer (pH 7.2, containing 1 mM $MgCl_2$, 0.01% $NaN_3$, 0.01% SDS, 2 mM DTT and 0.5% Triton X-100). Further treatment of the 120,000 species with 50 mM DTT for 1½ minutes at 100°, and gel filtration on Ultrogel AcA-34 in the above 0.01 M Tris-HCl buffer yielded two oligomers of the molecular weights 85,000 and 38,000. Each of these components bound $^{125}$I-hCG specifically and eluted from Ultrogel AcA-34 by 10 mM Tris-HCl buffer (pH 7.2, containing 1 MM $MgCl_2$, 0.01% $NaN_3$ and 0.5% Triton X-100) as hormone-bound complexes of molecular weights of 125,000 and 92,000, respectively.

In another experiment, $^{125}$I-hCG was coupled covalently to the 5.9 million molecular weight aggregate, which was then dissociated into hormone-bound 185,000 molecular weight species, but treatment with 2% SDS, for 1½ minutes, at 100°. A 3,000 rpm supernatant thereof was applied to a column of Sepharose-6B and in addition the sediment was redissolved in 10 mM Tris-HCl buffer (pH 7.2, containing 0.5% Triton X-100) and then treated with 2% SDS for 1½ minutes at 100° C. followed by gel filtration on the same type column. In both instances, the 185,000 molecular weight species was obtained by elution with 10 mM Tris-HCl buffer (pH 7.2, containing 1 mM $MgCl_2$, 0.01% $NaN_3$, 0.1% SDS and 0.5% Triton X-100).

Treatment of the $^{125}$I-hCG coupled species with 50 mM DTT for 1½ minutes at 100° also yielded $^{125}$I-hCG-coupled oligomers of the molecular weights of 110,000 and 74,000 (corresponding to 70,000 and 34,000 molecular weight units after subtracting 40,000 for hCG). Treatment of the 85,000 and 38,000 molecular weight units with up to 150 mM DTT in the presence of 2% SDS for 1½ minutes at 100°, did not dissociate these units further into smaller molecular weight components. Hence, it is expected that the 70,000 to 85,000 and the 34,000 to 38,000 molecular weight species are probably the disulfide linked subunits of the 120,000 to 140,000 molecular weight component and may be the smallest intact polypeptide units which carry out the specific binding with hCG and hLH.

From the above experiments and discussion, the two lowest molecular weight units known at this time of the naturally-occurring receptor may be defined with respect to their freedom from hormone units, their molecular weight ranges of about 34,000 to 38,000 and about 70,000 to 85,000, respectively, their specific binding capability for hCG and their stability under the various conditions of treatment heretofore described. In turn, these basic units appear to be linked through covalent disulfide bonds into repeating units of about 120,000 to 140,000 molecular weight. At the present time, it is believed that one each of the two types of basic units join to form the 120,000 to 140,000 molecular weight unit. Variations in molecular weight determinations are believed due to the limitations of the disc gel electrophoresis and gel chromatography systems, including the number of different standard protein markers employed. However, the important determinations are that two different molecular weight subunits, each having specific hCG binding capability exist which in turn form the basic repeating building blocks of the receptor. The 120,000 to 140,000 molecular weight species is in a sense a repeating monomeric unit, two of which link to form a 240,000 to 280,000 molecular weight oligomer. A plurality of these oligomers are associated with one another to form the 5.9 million aggregates.

Amino acid and carbohydrate analyses were carried out on the electrophoretically pure receptor product and on some of the partially purified intermediate receptor products. Amino acid analysis was carried out by dialyzing 100 µg aliquots of receptor overnight against water, drying in vacuo and hydrolyzing with 100 ml of 5.7 N HCl at 110° for 24 hours. The hydrolysate was dried again in vacuo to remove any residual acid. The sample was dissolved in citrate buffer, and analyzed for amino acids on an automatic amino acid analyzer (Durrum, Model D-500).

The neutral sugar content of the hLH-hCG receptor was determined by methanolysis of the sugars, trimethysilylation and gas liquid chromatography. The hexosamine content was determined on the amino acid analyzer after a 4 hour hydrolysis of the sample with 5.7 N HCl. The sialic acid content of the purified receptor was determined by the thiobarbituric acid method.

The major amino acids found in the electrophoretically pure receptor are aspartic acid and glutamic acid. On a percentage basis, there is somewhat less of each in comparison with a sample purified by the sequential method of the Reference Example but substituting affinity chromatography for zone electrophoresis. The carbohydrate content of the electrophoretically pure receptor is approximately 10%. See Table 1 setting forth amino acid and carbohydrate analysis of three receptor materials. The number of each type of amino acid residue in the glycoprotein aggregate can be calculated from Table 1.

The electrophoretically pure glycoprotein receptor aggregate acts as an antigen when administered to test animals, such as rabbits, for production of antiserum. The various glycoprotein subunits of the aggregate, as disclosed hereinbefore, also elicit antigenic response in test animals.

TABLE 1

AMINO ACID AND CARBOHYDRATE ANALYSES OF THE bLN-bCB RECEPTOR

| Amino Acid | Ultrogel AcA-34* | Affinity Chromatography** | Zone-electrophorosis (without final immuno-affinity chromatography step) |
|---|---|---|---|
| | | 9/100 g Protein | |
| ASPARTIC | 8.7 | 9.4 | 9.1 |
| THREONINE | 4.0 | 5.6 | 5.3 |
| SERINE | 3.9 | 4.6 | 5.8 |
| GLUTAMIC | 13.6 | 12.6 | 12.1 |
| PROLINE | 9.0 | 8.7 | 5.2 |

TABLE 1-continued

AMINO ACID AND CARBOHYDRATE ANALYSES OF THE bLN-bCB RECEPTOR

| | Ultrogel AcA-34* | Affinity Chromatography** | Zone-electrophorosis (without final immuno-affinity chromatography step) |
|---|---|---|---|
| GLYCINE | 3.8 | 4.7 | 4.5 |
| ALANINE | 4.6 | 5.4 | 4.8 |
| VALINE | 6.0 | 5.1 | 8.3 |
| CYSTEINE | Not detectable | Not detectable | |
| Cysteic Acid | trace | 1.3 | 2.4[a] |
| METHIONINE | 1.5 | 1.7 | 2.3 |
| ISOLEUCINE | 4.9 | 5.5 | 4.4 |
| LEUCINE | 11.7 | 9.6 | 8.7 |
| TYROSINE | 3.4 | 4.3 | 4.9 |
| PHENYLALANINE | 5.1 | 6.0 | 5.0 |
| LYSINE | 7.3 | 6.9 | 7.0 |
| HISTIDINE | 3.6 | [e] | 2.8 |
| ARGININE | 7.5 | 7.6 | 7.4 |
| Carbohydrate | | | |
| Fucose | Not detectable | | Not detectable |
| Mannose | 1.2 | | 1.1 |
| Galactose | 0.7 | | 1.6 |
| N-acetyl-glucosamine | 1.1 | | 3.7 |
| N-acetyl-galactosamine | 0.3 | | 2.6 |
| Sialic acid | 0.5 | | 1.9 |

[a]Determined on a separate aliquot after performic acid oxidation
[e]Eluted with detergent
*Intermediate sample of Reference Example type sequence up to and including the chromatographic step using Ultrogel AcA-34 but prior to further purification
**Reference Example type sequence carried out up to the chromatographic step using Ultrogel AcA-34 and followed by affinity chromatography instead of zone electrophoresis The most preferred receptor purification method involves the steps of:

(1) homogenizing a receptor source material in an aqueous medium to disperse the receptor in a liquid aqueous fraction;

(2) separating membrane-bound protein containing the receptor from the liquid aqueous fraction;

(3) dispersing the membrane-bound protein in an aqueous medium and extracting the aqueous medium with an organic solvent in which lipids are soluble to remove lipid from the aqueous phase;

(4) separating the aqueous phase containing the receptor from the remainder of the product of step (3) and concentrating the aqueous phase; and (5) fractionating the aqueous phase based upon molecular weight to remove inert proteins and concentrating the receptor fraction.

It is preferably in the present invention that the process further comprises the steps of:

(6) subjecting the receptor fraction to electrophoresis to separate said fraction from other remaining protein fractions; and (7) purifying the receptor fraction by subjecting it to immunoaffinity chromatography.

REFERENCE EXAMPLE 2

Receptor Purification

FIG. 1 is a flow diagram of the most preferred receptor purification method of the present invention which is described in detail below.

A batch of 1200 g of fresh bovine ovaries stored at −60° C. were thawed. Corpora lutea (200 g) were dissected and homogenized with 1500 ml of 10 mM Tris-HCl buffer (pH 7.2, containing 20% glycerol, 1 mM $MgCl_2$, 0.01% $NaN_3$ and $10^{-6}$ M leupeptin). The homogenate was centrifuged at 164×g for 30 minutes to remove cell debris, and to recover more than 90% of protein hormone binding activity. The supernatant was further centrifuged at 16,300×g at 4° C. for 2½ hours. Almost 30% of proteins with 80% of hormone-binding activity were sedimented, and 70% of proteins with 20% of hormone-binding activity was removed in the supernatant which was discarded. The LH-hCG receptor in the sediment was solubilized in 1,000 ml of 10 mM Tris-HCl buffer (pH 7.2, containing 1% Triton X-100, 1 mM $MgCl_2$, 0.01% $NaN_3$ and $10^{-6}$ M leupeptin) by sonicating three times for 10 seconds each time at pulses of 50 watts followed by stirring in ice for 1 hour. Up to 50–60% of proteins were solubilized with 80% recovery of the LH-hCG binding activity. To remove the free lipids from the crude receptor solution, 500 ml of chilled redistilled petroleum then was mixed with the solubilized receptor. After stirring for 30 minutes at 4° C. the petroleum ether treated receptors was centrifuged at 16,300×g for 1 hour at 4° C. The soluble LH-receptor was recovered in the aqueous layer.

The aqueous layer containing soluble LH-hCG receptor was then concentrated through a PM-30 membrane to reduce the volume to about 300 ml, then applied to a 9×90 cm column of Sepharose-6B equilibrated with 10 mM Tris-HCl buffer (pH 7.2, containing 0.5% Triton X-100, 1 mM $MgCl_2$, 0.01% $NaN_3$ and $10^{-6}$ M leupeptin) at 4° C. The column was eluted with the same buffer. The soluble LH-hCG receptor was separated into three major protein fractions by gel filtration on Sepharose-6B. The fractions were analyzed for protein concentration and tested LH-hCG binding activity. Unretarded fraction I contained most of the LH-hCG receptor with protein recovery of about 14%. Fraction II and III contained the majority of proteins without hormone-binding activity. Therefore, gel filtration on a column of Sepharose-6B was an effective step to remove inert proteins.

Fraction I from the Sepharose-6B column was concentrated five fold by ultrafiltration through a PM-30 Amicon filter to a protein concentration of 1.0 mg/ml, and mixed with equal volume of 30% polyethylene glycol 6,000 (PEG) and stirred for 20 minutes at 4° C. The precipitate was recovered by centrifugation at 16,000×g for 1 hour at 4° C. The precipitate was redissolved in Tris-HCl buffer (pH 7.2, containing 0.5% Triton X-100 and 1.0 M NaCl) by stirring for 1 hour at 4° C. and for 20 minutes at room temperature. The solubilized fraction was applied to a 5×50 cm column of Ultrogel AcA-22 (Pharmacia) equilibrated with Tris-HCl buffer. The column was eluted with the same buffer at a flow rate of 10 ml/20 minutes in a refrigerated fraction collector. The fractions were pooled and analyzed for protein content and hCG binding activity. The active fraction I from the Ultrogel AcA-22 column was precipitated at a final concentration of 15% PEG. The precipitate was dissolved in Tris-HCl buffer (pH 8.3, containing 0.5% Triton X-100) to yield a protein concentration of 3–6 mg/ml.

Then, zone electrophoresis was performed to discriminate proteins based on charge. More specifically, a 4×35 cm cellulose column was equilibrated with 10 mM Tris-HCl buffer (pH 8.3, containing 1 mM $MgCl_2$, 0.01% $NaN_3$ and 0.5% Triton X-100). An aliquot of up to 200 mg protein of the LH-hCG receptor fraction I from Sepharose-6B was applied onto the cellulose column in a volume of 20–30 ml. Electrophoresis was performed at a constant voltage of 30 v for 76 hours at 4° C. At the end of the electrophoresis, the column was eluted with the same buffer at a flow rate of 5 ml per 20 minutes. Each protein fraction was pooled on the basis of absorbency of 280 nm and the $^{125}$I-hCG-binding activity. Only fraction II contained the receptor with hormone-binding activity which was concentrated by ultrafiltration through a PM-30 Amicon filter and stored in a lyophilized state at 4° C. until use.

AcA-22 chromatography was repeated as described above to remove impurities (buffer salts and excess Triton X-100) resulting from the zone electrophoresis.

Next, affinity chromatography was performed to verify the purity of the receptor. More specifically, highly purified hCG was covalently linked to CNBr-activated Sepharose-4B by the procedure recommended by the supplier (Pharmacia). Fraction II from the zone electrophoresis column, containing the LH-hCG receptor, was applied to the affinity column and the column was eluted at a flow rate of 0.5 ml/minute. The column was washed with the buffer until no proteins were eluted. The LH-hCG receptor was eluted with 10 mM Tris-HCl buffer (pH 4.0 (adjusted with acetic acid), containing 0.5% Triton X-100, 0.5 M NaCl). The column was eluted at a flow rate of 4 ml/10 minutes. Each fraction was immediately adjusted to pH 7.2 with 1 M NaOH. Fractions containing LH-hCG receptor were pooled and concentrated.

Analysis of the purified LH-hCG receptor from the affinity chromatography on SDS-polyacrylamide gel electrophoresis as described above revealed a single band attesting to the purity of the LH-receptor.

The second antigen component used herein is hCG. Although it may be possible to use naturally occurring hCG, preferably the B subunit, or a derivative or fragment thereof, in modified or unmodified form, is employed to reduce generation of antibody cross-reactive with hLH and/or other hormones which include the non-specific β-subunit. The hCG antigen can be obtained commercially, purified and the hCG-β prepared as known in the art. For example, see the description of Bahl, U.S. Pat. No. 4,310,455, beginning at column 4, line 23, and the procedures of Swaminathan and Bahl, Biochem. Biophys. Res. Comm., 40:422, 1970 and Bahl, Hormonal Proteins and Peptides, C. H. Li, ed., Acad. Press, page 170, 1973, referenced in said Bahl patent.

Although the invention has been disclosed with respect to the preferred use of the electrophoretically homogeneous receptor and/or subunits thereof, it should be understood that various receptor derivatives and fragments could be employed in the practice of the present invention as long as the particular derivative or fragment utilized still possesses the ability to elicit an antigenic response in the production of antibody to the hCG receptor site. Various chemical and enzymatic modifications and digestions can be employed to prepare receptor derivatives and fragments. In a similar manner, the preferred hCG-β employed as a reagent herein can be utilized as such, or in the form of a derivative or fragment thereof, particularly those disclosed in the prior art as having increased immunospecificity and/or increased antigenic properties. Chemical modification, enzymatic cleavage and the like can be carried out prior to conjugation with the purified hLH-hCG receptor. For example, the various alkylated hCG-β derivatives of Bahl, the further purified hCG-β of Talwar and the like can be employed in the present invention. The receptor or its oligomeric components or after their modification may have preferential sites, specific only for hCG alone.

Many different procedures are known for linking or complexing a hormone-type unit with a protein. Basically, any of the procedures known in the prior art for conjugating one protein with another can be employed herein. Covalent bonding, ionic bonding, Van de Waals forces and the like, alone or in combination, can be employed to form the hCG β-receptor antigen conjugate or complex. What is needed is to insure that where the dual function antigen is desired, that the coupling mechanism utilized is sufficient so that substantially all of the antigen material can circulate intact. This is particularly important where a passive immunization technique is to be employed. That is, through the use of the dual function conjugated antigen, a dual function antibody can be secured and then utilized as a contraceptive vaccine.

Thus, conjugation or linking of hCG, preferably hCG-β or a derivative or fragment thereof, with the receptor can be carried out utilizing any standard procedure, such as by reacting hCG-β and the receptor in aqueous medium with one of the bi-functional cross linking reagents disuccinimidyl suberate (hereinafter "DSS"), dithiobis (succinimidyl propionate) and N-succinimidyl 3-(2-puridylthio) propionate. See Carlsson et al., "Protein-Thiolation and Reversible Protein-Protein Conjugation", Biochem. J., 173:723 (1978), and Rebois et al., "Covalent Cross Linking of Human Chorionic Gonadotropin to Its Receptor in Rat Testes", Proc. Natl. Acad. Sci. U.S.A., Volume 78, No. 4, p. 2086 (April 1981). Other techniques that could be used would be to carry out the reaction utilizing as the linking agent glutaraldehyde according to Avarameas, S., Immunochem., 6:43 (1969) or with a water soluble carbodiimide according to Cuatracasas, P. and Anfinsen, C. B., Methods. of Enzymolopy, XXII:343 (1971). Other procedures using reagents such as ethylchloroformate, bifunctional arylhalides, such as 1,3 or 1,4 di fluoro- or dichlorobenzene, 2,4 difluoro- or dichlorotoluene, 4,4 difluoro- or dichloro-bi-phenyl and the like, 1,5-difluoro-2,4-dinitrobenzene, bifunctional isocyanates, such as toluene 2,4-diisocyanate, toluene 2,6-diisocyanate , 4,4$^1$-diisocyanatodiphenylmethane, hexane 1,6-diisocyanate and the like, and bifunctional acylating agents such as di-acid halide, carboxylic dianhydrides, dicarboxylic acids, and esters and diamides, and imiidoesters, etc. may also be used.

At the present time, the preferred conjugation procedure utilizes DSS.

REFERENCE EXAMPLE 3

Formation of hCG-Receptor Unit

In this experiment, hCG-β and the electrophoretically homogeneous 5.9 million molecular weight receptor aggregate were utilized. hCG-β and the receptor were separately suspended in phosphate buffered saline at a concentration of approximately 1 milligram of protein per milliliter. DSS was dissolved in dimethyl sulfoxide at a concentration of 50 mM (1.8 mg DSS/100 ml), the solution of DSS being added to a protein suspension containing 1.5 mg of hCG-β and 1.0 mg of the receptor so that the concentration of dimethylsulfoxide in the final solution is 2%. The mixture was incubated at 25° C. for 15 minutes. Any non-conjugated hCG was dissociated by dilution of the sample with an equal volume of 4 M $MgCl_2$. Then, a second incubation was carried out at 4° C. for 10 minutes, followed by centrifugation at 5,000×g for 15 minutes.

The solution was subjected to Sepharose-6B chromatography using a column of 1×60 cm. The Sepharose-6B column was eluted with 0.01 M Tris HCl buffer (pH 7.2, containing 1 mM $MgCl_2$, 0.01% $NaN_3$ and 0.5% Triton X-100). Collection was at a flow rate of 1.5 ml/tube/15 minutes. Various fractions were analyzed for hCG-β presence and receptor presence by utilizing standard radioimmunoassay techniques for hCG-β and standard radioreceptor assay techniques for the receptor. In this experiment, a fraction comprising tubes 22 and 23 contained significant hCG-β and receptor antigenic activities. Remaining collected fractions possessed binding activity for hCG-β but did not possess binding activity for the receptor, indicating the separation of excess hCG-β from the conjugate.

As discussed above, the hCG and receptor antigens, separately or in conjugated form, may be used to produce antibodies to both hCG and the receptor either in lower animals, whereby an antiserum useful as a vaccine in humans or animals is produced, or the antigen materials may be administered directly to humans or animals, in which case the antibodies would be produced in humans or animals. In either case, the antiserum is being utilized for prevention or termination of pregnancy.

The antiserum can be prepared by conventional procedures utilized in the preparation of other types of antibody serum in lower animals. That is, a host animal such as a horse, goat, sheep, rabbit, monkey, pig or the like is injected with antigen on a regular basis until the blood thereof contains the desired level of antiserum. The injection schedule for the antigen is not critical, it may be injected as often as practical. In practice, injection every other week usually proves to be satisfactory. Longer or shorter periods between injections are, of course, possible. The dosage of antigen is, of course, proportionate to the weight of the host animal. The minimum dosage is that required to induce an antibody response in the host, while the maximum is that at which no adverse side reactions occur. In practice, dosages from about 2 μg/kg to about 50 μg/kg of body weight will usually prove satisfactory. The injections are continued until the desired antisera level in the blood serum is attained. Generally, an antisera titer of from 1:5,000 to 1:10,000 would be considered satisfactory.

When the desired titer is achieved, a quantity of blood is withdrawn from the host animal. The serum portion of the blood is then recovered. The quantity of blood removed is a function of the total volume of blood in the host animal. Generally, up to about 12 volume percent of the blood may be removed at any time without the host animal suffering excessive adverse effects. Thus, if the host animal is a rabbit, from about 20–40 ml blood will be removed.

The serum can be recovered by simply allowing the blood to coagulate and then decanting the blood serum. Various conventional purification steps can be utilized.

A typical immunization procedure using rabbits is as follows: 100 micrograms of the antigen material in 0.5 ml saline is mixed with an equal volume of Freund's complete adjuvant to form an emulsion. The emulsion is injected at 10–20 sites intradermally and subcutaneously. The injection schedule is repeated every other week using one-half the original amount of the antigen materials at two sites subcutaneously or intramuscularly. The serum samples are collected every other week from an ear vein and are tested for binding using radioactive assays for both hCG and the receptor. One regimen for raising the antibody is that disclosed in Avarameas et al., *Immunochem.*, 6:53 (1969).

In using the vaccines of the present invention to prevent or terminate pregnancy, either the antibodies themselves are administered to a female or the antigen(s) are administered to a female to provoke the formation of antibodies therein. In either case, antibodies are present in the female to effectively neutralize hCG and also to prevent hCG from interacting with the hCG-hLH receptors of the corpus luteum and of the placenta. The prior art, such as the Bahl and Talwar patents discussed hereinbefore, disclose appropriate techniques and levels of hCG-β antigen to be utilized in contraceptive vaccine regimens. Similar levels of administration are contemplated herein.

The hCG-receptor unit or the receptor alone can be employed when administered in a pharmaceutically effective amount as a contraceptive vaccine. Generally, a pharmaceutically effective amount will vary depending upon the age, weight and species to which the hCG-receptor unit or receptor is administered. Generally, a dosage in the range of 100 μg to 200 μg is employed, preferably 50 μg to 100 μg.

In preferred embodiments of this invention, the antibody levels maintained in the female would be less than that required with the hCG-β vaccines of the prior art because of the dual function of some of the antibodies in the present invention, that is not only to neutralize hCG but also to block receptor sites. The dual action will compensate for the low titer of the antibody and will permit negligible cross reaction with hLH. The hLH excess during the preovulatory phase should overcome the immunological block, and it is expected that ovulation will not be impaired.

As discussed above, the present invention is not limited to a contraceptive vaccine for humans, i.e., it is also applicable for veterinary use as a contraceptive vaccine in dogs, cats, cows, sheep, pigs, etc.

In the vaccine embodiments of the present invention, the antigens and/or antibodies used are administered in a pharmaceutically acceptable carrier, such as the various aqueous and lipid media, such as sterile saline, utilized for preparing injectables to be administered intramuscularly and subcutaneously. Conventional suspending and dispersing agents can be employed.

Other means of administration, such as implants, for example a sustained low dose releasing bio-observable pellet, will be apparent to the skilled artisan.

It is preferable in the present invention to employ silastic implants containing the receptor unit or receptor of the present invention. These implants can be used subdermally with lyophilized powder of the receptor unit or receptor. Body fluid such as plasma can pass through the silastic implant and pick up, as a carrier, small amounts of the receptor unit or receptor.

REFERENCE EXAMPLE 4

Formation of Silastic Implants

The silastic implants of the present invention can be prepared by, for example, solubilizing highly purified receptor in 10 mM Tris-HCl buffer (pH 7.5, containing 0.5% Triton X-100) in an appropriate concentration. Silastic tubing cut into 0.3 cm×10 cm pieces can be slit horizontally on one side to allow the tubing to be pried open like a sheet. The sheet can roll back into the form of tube again. An elastic needle heated at 90° C. can be used to pierce 10–20 pin holes in the tubing to allow the material to flow out easily from the implant under the skin. The inner volume ($mm^2$) of the silastic tube can be calculated from the formula $\pi \times r^2 \times h$. The concentration of the receptor solution can be adjusted such that the volume (mm²) of the silastic tubing contains about 2.5 mg of receptor. The receptor solution can be sterilized by ultrafiltration through a 0.45 Amicon filter prior to use. Silastic tubes of 0.3 mm×10 mm can be placed in a vial in an upright position tightly against each other so as not to tilt. The receptor solution can then be poured into the vial to cover the silastic tubing. Any air bubbles trapped in the tubing can be removed by suction with the aid of a syringe to allow the silastic tubing to be completely filled with the receptor solution. The solution can then be frozen and lyophilized under sterile conditions. The resulting silastic implant will contain about 2.5 mg of the lyophilized receptor. The implants can be stored individually in free load treacheries for implantation at 4° C. in a dessicator under sterile conditions. The silastic implants of the present invention can last from 6–12 months in a human or animal and can be replenished with fresh lyophilized powder of the receptor unit or receptor if necessary.

With decaying titers of antibody employed in the present invention or with the implants employed in situ in the present invention, the hormonal profiles and the return of cyclicity in the menstruation and perineal swelling can lead to the reversibility of infertility brought about by the contraceptive of the present invention.

Although the present invention has been disclosed with particular reference to contraceptive use in human and animal breeding, the antigens used herein, particularly the conjugate, would also have utility in other areas related to the treatment of gonadotropic hormone dependent cancers and the like, the diagnostics and management of reproduction, namely gonadal function, ovulation, abnormal pregnancy, disorders of hormonal production and spermatogenesis in the male.

Antibodies can be made to the LH receptor alone, such as S1, S2, S3 and S4 described herein. For example, as described hereinbelow, antibodies directed to the LH receptor can inhibit testosterone secretion by isolated testicular cells. Thus, antibodies directed to the LH receptor can be used to control the secretion of sex steroid hormones in vivo. For example, known conditions that result from or result in excessive circulating sex steroid hormones include prostatic hyperplasia, precocious puberty, gonadal neoplasms, pattern baldness, hormone-responsive benign prostatic hypertrophy, pseudohermaphroditism, polycystic ovary syndrome, Stein-Leventhal syndrome and the like. Of particular interest are conditions related to androgen excess.

The sex steroid hormone excess can arise from disturbances to gonadal cells or other cells that acquire or become capable of responding to LH. Certain malignancies such as breast cancers, are responsive to sex steroid hormones. Thus, control of sex steroid hormone secretion may serve to temper growth and/or metastasis of hormone-responsive malignancies. Essentially, any circumstance in which the levels of sex steroid hormones need to be controlled can be manipulated by the administration of LH receptor antibodies.

Epiphyseal closure of the long bones is sex hormone responsive and thus Lh-R antibodies may be used to influence the timing of closure. Blocking the LH-R and thereby reducing steroid hormone production will serve to delay closure and promote further increase of stature.

Whereas the discussion above relates to antibodies that exert an antagonistic effect, antibodies also can have an agonistic effect, that is mimic an effector molecule. Thus, for example, an antibody may on binding to a membrane bound receptor, activate rather than block said receptor thereby resulting in expression or enhanced expression of the normal responses found when the proper ligand engages the receptor.

Accordingly, an anti-LH-R antibody can serve to up-regulate steroid hormone secretion by activating the LH receptor on binding thereto, thereby mimicking LH and yielding cellular responses normally observed when LH engages LH-R.

Thus, agonistic LH-R antibodies can be used in conditions characterized by low or fluctuating steroid hormone levels, such as the climacteric in human females, cases of LH deficiency or LHRH deficiency and the like.

The agonistic and antagonistic antibodies can serve to manipulate and regulate menarche and climacteric.

It is possible to employ polyclonal antibodies in the practice of the instant invention. When specific antagonistic and agonistic functions are desired, a polyclonal antiserum can be absorbed to render it "monospecific" or at least lacking in antibodies directed to determinants found on the absorbant, generally whole cells.

On the other hand, it is possible to use monoclonal antibodies in the practice of the instant invention. Recovery of antibodies with specific function is enhanced using the purified receptor of the instant invention as antigen. Antibodies directed to specific determinants can be obtained in high titer and in essentially unlimited quantities.

Administration of the LH antibody is obtained using art-recognized techniques for the administration of biological materials. Accordingly, the antibodies can be administered intravenously, intramuscularly and the like. The antibodies can be suspended in suitable physiologic buffers containing various non-critical elements such as preservatives, salts, stabilizers and the like. The artisan can refer to a variety of treatises and text books in the pharmaceutic arts for guidance. The appropriate dosages and dosage regimen of the antibody therapy can be determined by extrapolating from suitable in vitro or animal studies or determined empirically from clinical studies.

REFERENCE EXAMPLE 5

Antigenicity of LH-R has been demonstrated by the production of polyclonal antibodies against murine LH-R in rabbits (Luborsky and Behrman, 1979, supra; and Rosemblit et al., 1988, supra); against bovine LH-R in rabbits (Dattatreyamurty et al., J. Biol. Chem. pp. 3140–3158, 1983); and, in non-human primates (for example, see Pal et al., J. Repro. Immunol. 21, 163–174, 1991). The production of monoclonal antibodies against murine luteal membrane (Podesta et al., 1983, supra) and porcine LH-R (Vuhai-Luuthi et al., 1990, supra). However, it has not been possible to use a purified antigen source to make high titer, high affinity antibodies to the receptor until the invention disclosed herein. Now pure receptor can be used to generate antibodies thereto.

Eight week old BALB/c mice, (Jackson Lab., Maine) were immunized with purified LH-R using two protocols. In Protocol "A" an aliquot of 100 ug protein in 0.1 ml phosphate buffered saline (PBS) was emulsified with an equal volume of complete Freund's adjuvant (CFA) (Sigma) and injected intraperitoneally. A second injection of the same dose was given after ten days. A final booster injection of 400 ug protein was given after four weeks.

In Protocol "B", mice were injected first subcutaneously (s.c.) with 100 ug purified LH-R in 0.1 ml PBS emulsified with an equal volume of CFA. Two additional s.c. injections of 100 ug antigen each were given at a two weeks interval. Booster injections of 50 ug antigen in PBS were given intravenously daily for three consecutive days prior to the recovery of splenocytes from the immune mice. Serum or immunoglobulins derived from mice, injected only with CFA and PBS (1:1), were used in control experiments. Prior to each injection, 100 ul of blood was drawn from the tail vein or the retroorbital plexus.

The antibody titers in serum samples were determined by a modification of an enzyme linked immunosorbent assay (ELISA) (Engvall, Meth. Enz. 70, 419, 1980). The antigen was diluted in PBS, without $Ca^{++}$ and $Mg^{++}$ ions, to a concentration of 50 ug protein/ml and diluted six times in doubling dilution to yield a final dilution of 1:64. To bind the antigen to a 96 well flat bottom microtiter plate (Immulon), 100 ul of the antigen solution was added to all 12 wells of Row A. All the wells of Rows B to G received 100 ul of each of the six dilutions of the antigen. Row H received 100 ul of PBS alone in each well. The plate was sealed with acetate plate sealer (Dynatech) and incubated overnight at 4° C. Each well was washed three times with 200 ul of PBS containing 0.05% Tween-20 (PBS-Tween). The plate then was treated with 1% bovine serum albumin (BSA) in PBS-Tween, for two hours at room temperature to block non-specific binding sites. Finally, the plate was washed three times with PBS-Tween.

Thirty ul of serum samples were made to 1.5 ml with PBS, containing 0.5 mg BSA/ml, to yield a starting dilution of 1:50 and diluted serially to a final dilution of 1:102,400. To bind the antibody to the antigen, each well of row 1 of the above plate received 100 ul of the 1:50 dilution and rows 2–11 received 100 ul of each dilution of the serum. The plate was incubated for 2 hours at room temperature, after which it was washed 3 times with PBS-Tween.

For the detection of the bound antibody, 100 ul of an anti-mouse antibody conjugated to horseradish peroxidase (HRP) and diluted to 1:500 with PBS-Tween containing 1% BSA, were added to each well. The plate was incubated for 2 hours at room temperature and washed 3 times with PBS-Tween. A 100 ul aliquot of a freshly prepared solution of substrate, containing 0.04 mg O-phenylenediamine (Sigma) per ml of 0.05 M sodium citrate buffer of pH 6.0, containing 0.15 M sodium phosphate and 0.32 ul of 30% hydrogen peroxide, was added to each well. After a 30 minute incubation at room temperature, the reaction was stopped by the addition of 50 ul of 4 N sulfuric acid to each well and the absorbance at 490 nm was recorded in a Bio-Tek plate reader.

The fusion was performed as described by Goding (Monoclonal Antibodies: Principles and Practices, Academic Press, N.Y. 1986). Mice showing high titer of antibodies to LH-R, were sacrificed to recover splenocytes. Myeloma cells P3×63-Ag8653 (ATCC CRL 1560) were cultured in Dulbecco's modified Eagles Medium (DMEM), containing 20% fetal calf serum (FCS), 100 ug/ml streptomycin, 100 ug/ml penicillin, 100 ug/ml Fungizone® and 20 mM glutamine. The myeloma cells were kept in DMEM with antibiotics and without FCS in aliquots of $10^7$ cells. Splenocytes from each mouse were suspended in 3 ml DMEM and fused with $10^7$ myeloma cells by dropwise addition of 1 ml of 30% polyethylene glycol (PEG) in Dulbecco's PBS, pH 7.3 using known procedures. After fusion, 60 ml of DMEM-FCS-hypoxanthine-aminopterin-thymidine (HAT) medium was added. Aliquots of 100 ul of the hybridoma suspension were plated in a 96 well plate containing 100 ul DMEM-FCS-HAT medium and incubated at 37° C., under 5% $CO_2$ and 95% $O_2$. After 2 days the cells were fed with fresh HAT medium. Two weeks later the hybridomas were kept in hypoxanthine/thymidine (HT) medium. In Protocol B, Sp2/10 cells were fused as controls.

One week after fusion, the LH-R antibody-secreting hybridomas were detected by ELISA, using anti-mouse HRP conjugate, at 1:350 dilution and a starting antigen concentration of 12.5 ug/ml. From mice immunized according to protocol A, twelve of sixteen hybridomas showed optical densities greater than controls or greater than the positive controls. Each well of the hybridomas producing a high titer antibody was split into four wells of a 96 well plate. Each of the four wells was transferred into a 9.6 $cm^2$ six well plate, then into a 25 $cm^2$ flask, and finally, each 25 $cm^2$ flask into a 75 $cm^2$ flask. The hybridoma supernates were stored frozen at −70° C.

The LH-R antibody producing hybridomas obtained from the mice immunized according to the Protocol B were cloned by limiting dilution. A single hybridoma cell was lodged in each well and further subcloned to ensure monoclonality. Hybridomas, producing high titer antibodies, were further grown as ascites by injecting (i.p.) 4×$10^6$ cells into one month old BALB/c mice, previously primed with 5 ml of either pristane or incomplete Freund's adjuvant. Ascites fluid was collected by aspiration with a needle, centrifuged to remove cell debris and stored at −70° C. Hybridoma supernates and ascites fluid were analyzed for protein concentration by a Biorad® Kit. Four LH-R mAb's were obtained.

LH-R antibodies were detected by ELISA and further analyzed either by the receptor binding inhibition assay using bovine corpora lutea plasma membranes (Saxena, in Methods in Receptor Research, Blecher, ed., Marcel Dekker, Inc. N.Y. 1976), or by the inhibition of testosterone production by hCG stimulated rat Leydig cells (Van Damme et al., Acta Endo. 77, 655–672, 1974). Dilutions of ascites fluid of similar optical density in ELISA, indicating similar antibody concentrations, were used in the assays.

A saturated solution of ammonium sulfate (pH 7.8) was added dropwise to each of the slowly stirring 50 ml aliquots of supernates of hybridoma until the solution turned turbid. The solution was stirred for 2 hours and centrifuged at 3,000 rpm for 30 minutes. The supernate was decanted and the precipitate was dissolved in PBS to the original sample volume. The solution was again treated with saturated ammonium sulfate solution, as above. The precipitate was recovered by centrifugation, dissolved in 20 ml of PBS, and dialyzed (range 12–14,000 MW) against PBS, until the dialysate was void of ammonium sulfate ions as determined by 1% barium chloride solution. Ammonium sulfate precipitates of hybridoma supernates were analyzed for antibody titer and isotype as well as individually purified by column chromatography (Stanker et al., J. Immunol. Meth. 76, 157–169, 1985). Hydroxylapatite (HPHT, Biorad), hydrated in 0.1 M sodium phosphate buffer of pH 6.8, was packed into a 1×50 cm column. The ammonium sulfate precipitates were dissolved in and dialyzed against the above buffer. A sample volume of 15 ml was applied to the column. The column was eluted with a stepwise gradient of sodium phosphate.

Fractions were concentrated by Centricon® to, approximately, 4 ml. Each fraction was analyzed for protein concentration, for LH-R antibodies, for isotype as well as, by sodium dodecyl sulfate-polyacrylamide gel electrophoresis (SDS-PAGE) in a discontinuous system, at pH 9.0, with 5% acrylamide as the stacking gel at pH 6.8 and 10% acrylamide as the separating gel (Laemmli, Nature, 227, 680–685, 1970).

Ascites fluid containing mAb's obtained from Protocol B was purified by ammonium sulfate precipitation.

Sixteen monoclonal antibodies directed to LH-R were obtained in the foregoing experiments. The cells lines are identified as S1 though S16. Cell lines S1, S2, S3 and S4 from protocol A were deposited on 5 May 1992 with the American Type Culture Collection.

REFERENCE EXAMPLE 6

*E. coli*, such as strain Y1090, Y1090 is streaked out on LB plates containing 50 µg/ml ampicillin. A single isolated colony is picked from the plate and is grown to saturation in LB broth plus 0.2% maltose at 37° C. with aeration. The concentration can be determined by reading the optical density.

A bovine expression library, such as a lambda gt11 ovary cDNA library obtained from Clontech, Inc. (Palo Alto, Calif.), is used. The titer of the library can be determined by plating different amounts in *E. coli* (Y1090) on LB plates.

For immunoscreening, in each of three tubes, 0.2 ml of the plating bacteria is mixed with 0.1 ml of SM buffer containing about $3 \times 10^4$ pfu of the bacteriophage expression library. The infected bacteria are incubated for 20 minutes at 37° C. 2.5 ml of molten top agarose are added to each tube and the mixture is poured immediately onto an LB agar plate. Usually 2-day old plates that are dried for an additional 1–2 hours at 37° C. with the lids slightly open work well to avoid the top agarose from peeling off when removing the nitrocellulose filter. The infected plates are incubated for 3.5 hours at 42° C.

Nitrocellulose filters (free of Triton X-100, for example, Millipore HATF) are identified with a pencil. The filters are soaked in a solution of isopropylthio-B-D-galactoside (IPTG) solution (10 mM in distilled water) for a few minutes. Using blunt-ended forceps, the filters are removed from the solution and allowed to dry at room temperature on a pad of wipes.

The plates are removed from the incubator and quickly overlaid with the IPTG-impregnated nitrocellulose filters, without allowing the temperature of the plates to drop below 37° C. The plates are incubated for at least 4 hours at 37° C.

The lids are removed from the plates and the incubation is continued for a further 20 minutes at 37° C. to help prevent the top agarose from sticking to the filter rather than to the plate. The plates are moved to room temperature and each filter is marked in three asymmetric locations with a needle. The filters are peeled off the plates and immediately immersed in a large volume of buffer, for example, TBST (50 mM Tris, pH 7.9, 150 mM NaCl and 0.05% Tween 20). Any small remnants of agarose are rinsed away by gently agitating the filters in the buffer. The TBST is agitated gently to prevent the filters from sticking to one another. The plates are covered with plastic wrap and stored at 4° C. until the results of the immunologic screening are available.

The filters are transferred to a fresh batch of TBST containing 20% fetal calf serum and the buffer is agitated gently for a further 30 minutes at room temperature. (5 ml/82 mm filter). The filters are removed and rinsed in TBST.

The filters are transferred to fresh glass trays containing an IgG fraction purified from a polyclonal antibody to LH-R, a mAb to LH-R or a pool of mAB's to LH-R diluted in TBST (7.5 ml for each filter). When all of the filters are submerged, the solution is agitated gently on a rotary platform for one hour at room temperature. The filters are washed in three changes of TBST containing 0.1% BSA, 3 minutes each change.

The antigen-antibody complexes are detected, for example, by using a secondary antibody conjugated with HRP (horse radish peroxidase) (such as, a goat anti-rabbit IgG (H+L) antibody) that reacts with species-specific determinants on the primary antibodies. The bound antigen-antibody complexes then are detected by, in the case of HRP, immunoperoxidase staining (using, for example, the CLIK kit from Clontech Labs, Inc., Calif.).

Alternatively, the filters are removed to TBST containing biotinylated secondary antibody and incubated at room temperature for 30 minutes with gentle agitation. About 20 ul of the secondary antibody is used per 10 ml. The filters are washed in 3 changes of TBST, 3 minutes each change.

An avidin-biotinylated complex is prepared by adding 40 ul of avidin and 40 ul of biotin-HRP conjugate to 10 ml of TBST and incubating that mixture at room temperature for 30 minutes before use. The filters are transferred to TBST and incubated at room temperature for 30 minutes with gentle agitation. The filters are washed in TBS (no Tween 20), 3 minutes each change.

Peroxidase substrate solution is prepared by mixing 2 ml of 4-chloro-1-napthol (3 mg/ml) in methanol with 10 ml of TBS plus 0.01M imidazole. Five ul of 30% hydrogen peroxide are added to the solution, the solution is mixed and used immediately. The nitrocellulose filters are incubated in 5 ml of the peroxidase substrate solution per filter and the color is allowed to develop for approximately 30 minutes. The filters are washed with three changes of distilled water and allowed to air dry.

The locations of positive plaques are identified by laying a sheet of clear plastic wrap over the filters. The locations of the holes in the filters and the locations of antigen-positive clones are marked and the plastic wrap is labeled to identify the plates from which the filters are derived. A sheet of plastic wrap is placed on a light box and the plates containing the original bacteriophage lambda plaques are aligned on top of the wrap. The areas containing the positive plaques are identified and a plug of agar is removed from that site. The plug is transferred to 1 ml of SM buffer containing 2 drops of chloroform.

The bacteriophage particles are allowed to elute from the agar for several hours at 40° C. The titer of the bacteriophage is determined in the eluate and then replated so as to obtain approximately 3000 plaques per 90-mm plate. The plaques are rescreened as described above and the process of screening and plating is repeated until a homogenous population of immunopositive recombinant bacteriophage is obtained. Polyclonal antibodies, a monoclonal antibody or a pool of monoclonal antibodies can be used for the screening.

About $10^5$ pfu of bacteriophage (usually about 1/20th of a resuspended plaque) are mixed with 0.1 ml of plating bacteria and is incubated for 20 minutes at 37° C. Three ml of molten (47° C.) top agar/agarose (0.7%) is added to the tube, which is poured immediately onto a freshly poured and labeled 90-mm plate equilibrated to room temperature and containing 30–35 ml of hardened bottom agar. For best results, the LB bottom agar can contain about 0.3% glucose, 0.075 mM $CaCl_2$, 0.004 mM $FeCl_3$ and 2 mM $MgSo_4$.

The plates are incubated for 6–8 hours at 37° C. or until at the time of harvesting the plaques are touching one another, and the only visible bacterial growth is a gauzy webbing that marks the junctions between adjacent plaques.

The plates are removed from the incubator, 5 ml of SM/plate are added and is gently shakened at 40° C. overnight. The SM is harvested with a Pasteur pipette and placed in a 13 mm×100 mm polypropylene tube. One ml of fresh SM is added to the plate and the plate is stored tilted for 15 minutes to allow the fluid to drain into one area. Again the SM is removed and combined with the first harvest, vortexed briefly and centrifuged at 4000×g for 10 minutes at 40° C. The supernatant is recovered, one drop of chloroform is added and is stored at 40° C. The titer of the stock is about $10^{10}$ to $10^{11}$ pfu/ml.

The lysed cultures are cooled to room temperature and pancreatic DNAse I and RNAase are added, each to a final concentration of 1 ug/ml.

The solution is incubated for 30 minutes at room temperature to digest the nucleic acids liberated from the lysed bacteria.

Solid NaCl is added to a final concentration of 1M (29.2g/500 ml of culture) and dissolved by swirling. The solution is allowed to stand for 1 hour on ice. The addition of NaCl promotes the dissociation of bacteriophage particles from bacterial debris and is required for efficient precipitation of the bacteriophage particles from polyethylene glycol.

The debris is removed by centrifugation at 11,000×g for 10 minutes at 40° C. Solid polyethylene glycol (PEG 8000) is added to the supernatant, to a final concentration of 10% w/v (50 g/5000 ml of supernatant). The PEG is dissolved by slow stirring on a magnetic stirrer at room temperature.

The solution is allowed to cool in ice water for at least 1 hour to allow the bacteriophage particles to form a precipitate. The precipitated particles are recovered by centrifugation at 11,000×g for 10 minutes at 40° C. The supernatant is discarded.

The bacteriophage pellet is resuspended in SM (8 ml/500 ml of original supernatant). The walls of the centrifuge bottle are washed thoroughly since the precipitate of bacteriophage sticks to the sides.

The polyethylene glycol and cell debris are extracted from the phage suspension by adding an equal volume of chloroform adn vortexing for 30 seconds. The organic and aqueous phases are separated by centrifugation at 3000×g for 15 minutes ar 40° C. The aqueous phase, containing the phage particles, is recovered.

The volume of the aqueous phase is measured and 0.75 g of solid cesium chloride per ml of the suspension is added. The solution is mixed gently to dissolve and transferred to an ultracentrifuge tube that fits, for example, a Beckman Ti50 rotor. The tube is filled with SM containing 0.75 g/ml CsCl and centrifuged at 38000 rpm for 24 hours at 40° C. A bluish band of bacteriophage particles, seen more readily against a black backdrop with a light shining from above, is collected by puncturing the side of the tube.

Three molar sodium acetate (pH 7.0) is added to a final concentration of 0.3M and mixed well. Two volumes of ethanol are added and mixed. The solution is allowed to stand at room temperature for 30 minuntes. The thread-like bacteriophage DNA precipitate is removed from the solution on the outside of a Pasteur pipette and transferred to a microfuge tube containing 1 ml of 70% ethanol. The DNA is recovered by centrifugation at 12,000×g for 2 minutes at 40° C. in a microfuge. The supernatant is discarded carefully and the pellet of DNA is allowed to dry at room temperature and redissolved in an appropriate volume of TE buffer (pH 7.6).

Subcloning is performed using standard methods, for exmaple, using kits available commercially, such as from Boeringer Mannheim, and following the protocol and recommendations suggested by the manufacturer.

For example, a single colony of E. coli JM83 is removed from the LB plate and inoculated into 5 ml of LB liquid medium. The culture is incubated overnight at 37° C. with shaking.

Forty ml of LB liquid medium is inoculated with 0.4 ml of fresh overnight culture and incubated with shaking for about 2.5 hr at 37° C. to $A_{550}$=0.5 with JM83.

The cells are centrifuged for 10 minutes at 3,000×g in a pre-cooled rotor. The pellet is resuspended in 4 ml of ice-cold sterile $CaCl_2$ solution. The competent cells can be stored on ice for up to 24 hours.

Digestion of phage DNA with restriction endonucleases is done using standard procedures. For example, in a sterile microfuge tube, 2 ug of the DNA to be cloned is added to 2 ul of 10× restriction buffer. Nineteen ul of sterile water are added to the tube followed by 1–2 ul of about 2–10 units of enzyme. The solution is incubated for 1 hr at 37° C. TE buffer is added and the solution is extracted once with 200 ul of phenol/chloroform/isoamyl alcohol, and once with 200 ul of chloroform/isoamyl alcohol. Sterile LiCl solution and 750 ul of 95% ethanol are added and the solution is chilled for 15 min at −70° C. (in ethanol/dry ice mixture). The solution is centrifuged to 10 minutes and the supernatant is removed carefully and discarded. One ml of 70% ethanol is added to the precipitate and centrifuged for 5 minutes. The supernatant is removed, the precipitated DNA is dried briefly under vacuum and dissolved in buffer. An aliquot of 1 ul is checked on an 0.8% agarose gel for extent of cleavage.

Ligations and transformations are accomplished using standard procedures, for example, using kits available commercially, such as from Stratagene, San Diego, Calif. and BRL, Gaithersburg, Md., following the protocols and recommendations of the manufacturer.

Clones are sequenced using standard methods, for example, using any of the kits available commercially such as the Sequenase kit from USB using primers and reverse primers from the pUC18 kit of Boeringer-Mannheim, using either the chemical method or dideoxy method.

Immunoscreening of bacterial colonies is similar to that set forth above except that colonies are propagated on the membranes, the cells are lysed and the filters are blocked to control for the bacterial proteins, for example using a buffer comprising about 20% fetal calf serum or a cell lysate of non-transformed host cells.

By following such procedures, a number of clones carrying LH-R sequences have been identified. For example, a number of phage clones, such as, 3a1, 3a2, 3a4, 3a5, 3a6, 3a8, 3a3a, 3a3c, 3a3e, 3a3f, 3a5a and 8d1a, have been identified as LH-R clones.

The following examples are provided to illustrate the use of various aspects of the instant invention, such as, as a contraceptive vaccine, and are in no way intended to limit the scope of the present invention.

EXAMPLE 1

Active Immunization in Rabbits

Highly purified LH-hCG receptor was prepared as described in Reference Example 2. Three New Zealand white adult female rabbits of approximately 3 kg of body weight, designated as A, B and C, were boarded in an animal facility for active immunization against the receptor by multiple site subdermal injections to produce antibodies and observe the effect of endogenously produced antibodies on the reproductive functions of the rabbits. An aliquot of 100 μg protein equivalent of receptor suspended in 100 μl of 0.9% (w/v) saline was emulsified with 100 μl of complete Freund's Adjuvant and used for initial immunization by intradermal injections of 10–20 μl of the immunogen at multiple sites. Afterwards, aliquots of 100 μg of receptor emulsified in adjuvant as above were injected subcutaneously at four week intervals for a period of five and a half months. Rabbits were bled by the ear vein puncture at four week intervals after the first immunization. The blood was centrifuged at 3,400 rpm for 15 minutes at 40° C. The serum was separated and stored at −20° C. until analyzed.

The gamma-globulin fraction was isolated from the sera of immunized rabbits by Rivanol precipitation according to the method of Horejsi, J. S. et al., Acta Medica Scan., 155:65–70 (1956). After removal of the Rivanol the gamma-globulin fraction was concentrated in an Amicon ultrafilter using a PM-10 membrane. The gamma-globulin fraction was gel-filtered through a 3×30 cm column of Sephadex G-25 (fine) which was previously equilibrated in 0.1 M ammonium bicarbonate buffer of pH 8.5. The column was eluted with the same buffer. The gamma-globulin eluted in the unretarded protein fraction was lyophilized and stored at 4° C. The protein concentration in the gamma-globulin fraction was determined by the method of Lowry, C. H. et al., J. Biol. Chem., 193:265–275 (1951).

The antisera samples and the gamma-globulin fractions were examined for the presence of antibody by (1) the ability to specifically bind $^{125}$I-receptor, (2) the ability to inhibit specific binding of $^{125}$I-hCG to the receptor, (3) the ability to inhibit the production of testosterone by rat Leydig cells stimulated by hCG (Dafau, M. L. et al., J. Clin. Endocrinol. Metab., 39:610–617 (1974)), and (4) microplate enzyme immunoassays (Munro, C. et al., J. Endocrinol, pages 41–49 (1984)).

Separate aliquots of 1 ml each of the antisera were mixed on a Vortex with 0.5, 2.5, 5 and 10 μg of receptor protein as well as 6.25, 12.5 and 50 ng of hCG and incubated for 3 hours at 37° C. The incubates were centrifuged at 3,400 rpm in a Sorvall refrigerated centrifuge for 20 minutes.

The supernatants were separately collected and examined for specific binding with $^{125}$I-receptor as well as with $^{125}$I-hCG as discussed in detail below.

Highly purified LH-hCG receptor was labeled with high specific activity $^{125}$I-Na utilizing the chloramine-T method of Hunter, W. M. et al., Nature, 194:495–496 (1962) as follows. An aliquot of 5 μg of the receptor was dissolved in 50 μl of 0.1 M sodium phosphate buffer (pH 7.4, containing 0.1% Triton X-100) in a glass reaction vial. To the vial, 50 μl of 0.1 m of sodium phosphate buffer (pH 7.4), 0.5mCi of $^{125}$I-Na and 20 μl of chloramine-T of a concentration of 1 mg/ml, were added sequentially. After 1 minute of gentle agitation, 50 μl of a 2 mg/ml sodium metabisulfate solution was added to stop the reaction. An aliquot of 0.5 ml of 0.1 M sodium phosphate buffer (pH 7.4, containing 0.1% Triton X-100) was added and mixed to stabilize the reaction mixture. The mixture was filtered through a 1×30 cm column of Ultrogel AcA-34 equilibrated with 0.1 M sodium phosphate buffer (pH 7.4, containing 1.0% bovine serum albumin and 0.1% Triton) to separate the labeled receptor from the damaged protein and free $^{125}$I. The column was eluted into 0.5 ml fractions with the above buffer. Fractions were tested for specific binding with gamma-globulin isolated from antiserum against the receptor. Fractions with the maximum specific binding were pooled and further purified by gel-filtration again through another column of Ultrogel AcA-34 as described above. Fractions which showed the maximum specific binding were pooled and utilized.

In a competitive protein binding assay, rabbit anti-receptor antibody was examined for binding to the $^{125}$I-receptor and the displacement of the bound $^{125}$I-receptor by unlabeled receptor. More specifically, approximately 50,000 cpm of $^{125}$I-receptor in 100 μl of RIA buffer containing 0.05 M sodium phosphate buffer (pH 7.4, containing 0.1% bovine serum albumin (BSA), 0.01% NaN$_3$ and 0.2% EDTA) alone and in the presence of 1.5 μg receptor in 100 μl of RIA buffer were incubated overnight at 37° C. Specific binding was calculated from the decrease in the counts of the total binding in the presence of unlabeled receptor.

Inhibition of binding of $^{125}$I-hCG to the receptor was performed to examine the ability of anti-receptor antibody to inhibit binding of $^{125}$I-hCG to the plasma membrane receptor prepared from bovine corpora lutea and rat Leydig cells. More specifically, approximately $^{125}$ μg lyophilized protein aliquots of the plasma membranes were suspended in 100 μl of distilled water and incubated at 4° C. with approximately 50,000 cpm of the $^{125}$I-hCG in 100 μl of 10 mM Tris-HCl buffer (pH 7.2, containing 0.1% BSA, 1 mM MgCl$_2$, 1 mM CaCl$_2$, 0.01% NaN$_3$) for 60 minutes in the presence of 100 μl of various dilutions of antisera against the receptor or various amounts of gamma-globulin in 100 μl of 0.05 M phosphate buffered saline (PBS) (pH 7.4, containing 0.1% BSA, 0.01% NaN$_3$ and 0.2% EDTA). Parallel controls were performed using normal rabbit serum and normal rabbit gamma-globulin.

Inhibition of testosterone production by rat Leydig cells by anti-receptor antibody was carried out using Sprague-Dawley male rats between the age of 56–70 days with a body weight range of 250–350 gm. These rats were used to prepare the Leydig cells by the method described by Dufau, M. L. et al., J. Clin. Endocrinol Metab. 39, 610–617 (1974). More specifically, Leydig cells were suspended in medium 199 with 26 mM Hepes buffer, Hank's salts, L-glutamine (GIBCO), containing 0.125 mM of 1-methyl 3-isobutylxanthine (MIX, Sigma) and 0.1% BSA) and pre-incubated for 30 minutes at 34° C. under an air mixture of 95% O$_2$ and 5% CO$_2$ in a metabolic shaker at 150 cycles/minute. The Leydig cell suspension was centrifuged at 120×g. The supernatant was discarded and sedimented Leydig cells were resuspended in the same media containing 2% calf serum (GIBCO) at a concentration of 10 ml per testis and used as the source of receptor. The assay was performed at 37° C. and samples were incubated for 3 hours. Testosterone was measured by a RIA kit obtained from Diagnostic Products Corporation, Los Angeles, Calif.

Figure 2:
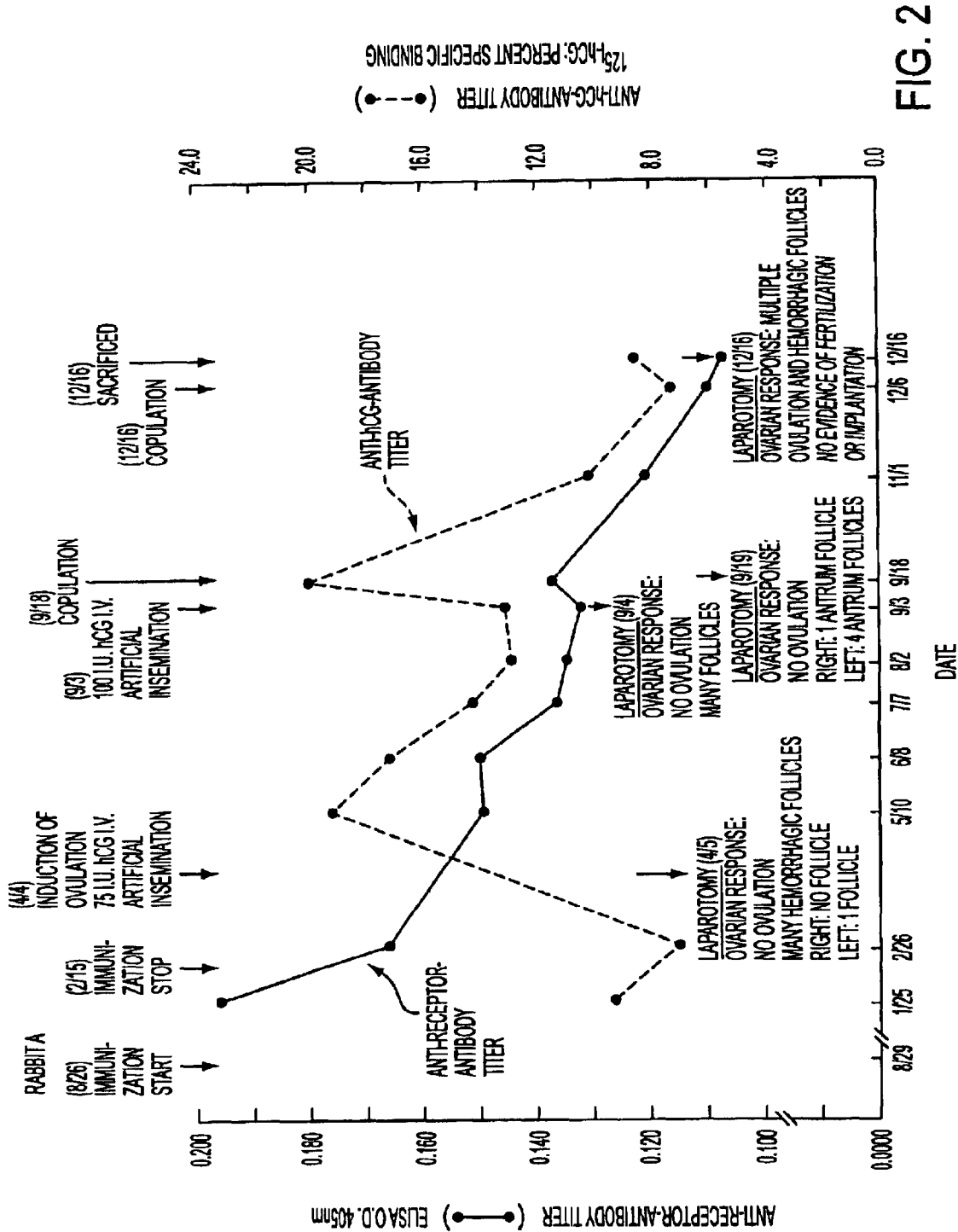
FIGS. 2 and 3 graphically illustrate the effect of endogenous anti-receptor antibody on reproductive functions in female rabbits.

The effects of active immunization against the hCG-LH-hCG receptor complex on the reproductive functions in rabbits, namely ovulation, fertilization, corpus luteum formation and implantation were observed in the presence of anti-receptor antibody in the blood circulation of rabbits. The rabbits were induced to ovulate and then artificially inseminated. Laparotomy was performed to observe follicular growth, ovulation, corpus luteum formation as well as implantation of the blastocyst at an appropriate time as described in FIGS. 2 and 3. Specifically, two months after the last immunization, 75 IU of hCG was injected into rabbit A and C via ear vein. The rabbits were immediately artificially inseminated with 2 ml of fresh semen obtained from the epididymis of a fertile male rabbit. The laparotomy was performed 20 hours after the induction of ovulation and artificial insemination. The ovaries were examined for folliculogenesis and ovulation. The status of the uterus was also examined in both the rabbits.

Rabbit C was sacrificed eight days after the laparotomy. Tissue from brain, lung, heart, thyroid, spleen, stomach, kidney, urinary bladder, ureter, liver, intestine, uteri, cervix and fallopian tube were removed and fixed in 40% formalin for histopathological examination to rule out any toxic effects of antibody against LH-hCG receptor.

Five months after the last immunization, rabbit A was again stimulated with 75 IU of hCG and inseminated as described above. Twenty hours later, a laparotomy was performed and rabbit A was again examined as described above. Two weeks later rabbits A and B were mated with two fertile male rabbits. Twenty-four hours later, rabbits A and B were subjected to laparotomy. Two weeks later another laparotomy was performed and rabbit B was examined for the status of ovaries, corpus luteum formation, evidence of fertilization and implantation. Periodically blood was collected from rabbits A and B and analyzed for antibody titers. The rabbits were subsequently observed to evaluate the reversal of ovarian function and fertility.

The sera samples of rabbits A, B and C obtained prior to immunization and periodically during immunization and after the cessation of immunization were analyzed for $E_2$, P and LH levels by RIA kits. The reagents were supplied by Nuclear Medical Systems, Inc., Newport Beach, Calif. LH levels in rabbit sera were estimated by a RIA method. Rabbit LH supplied by NIH (National Hormone and Pituitary Program, Baltimore, Md.) was iodinated by the chloramine-T method described above. Rabbit LH was used for iodination and as a standard.

Rabbits A, B and C showed the presence of receptor antibody in the serum collected during the fourth month subsequent to the first immunization. The antisera from rabbits A, B and C were then examined at four week intervals for specific binding with $^{125}$I-receptor as described above. The results demonstrated that the antibody showed an increasing titer with further immunization. One hundred µg aliquots of the globulin fractions isolated from the sera of rabbits A and C also showed a specific binding of 18.6 and 15.0 percent, respectively, with labeled receptor.

The gamma-globulin fractions prepared with antisera from rabbits A and C were pooled and examined for the ability to inhibit the binding of $^{125}$I-hCG to the receptor in crude plasma membranes, prepared from bovine corpora lutea and Leydig cells prepared from rat testis as described above. The results demonstrated that there was 31% inhibition of binding of $^{125}$I-hCG to bovine corpora lutea membranes by 100 µg of gamma-globulin as well as 67% and 85% inhibition in the case of rat Leydig cell membranes by 150 µg and 300 µg of gamma-globulin, respectively.

The presence of antibodies against the receptor was further demonstrated when 100 µg of gamma-globulin fraction caused a 41% inhibition in the production of testosterone by rat Leydig cells, stimulated by 50 mIU of hCG an described above.

The anti-receptor antibodies produced in the rabbits also demonstrated cross-reaction with $^{125}$I-hCG, indicating an elaboration of idiotypic antibodies.

Anti-receptor antiserum absorbed with 0.5 µg, 2.5 µg, 5 µg and 10 µg protein equivalent of receptor per ml serum, yielded a progressive decrease in the specific binding of the $^{125}$I-receptor, namely, 15.3%, 10.3%, 4.4% and 3%, respectively, as compared to 55.7% specific binding. It may be noted that binding of I-hCG to the unabsorbed and absorbed anti-receptor did not change binding with the unabsorbed anti-receptor antibody. The $^{125}$I-receptor bound to the absorbed anti-receptor anti-serum, was not displaced by the unlabeled hCG. These results further demonstrate that the anti-receptor antibody contained discrete and specific antibodies directed against the LH-hCG receptor. Similarly, after the absorption of the anti-receptor antisera with 6.25, 25 and 50 µg of hCG per ml, the specific binding of $^{125}$I-hCG to absorbed sera decreased to 44.8%, 34.3% and 20.2%, respectively. These observations suggest that the anti-receptor antisera contained a separate entity of antibody which specifically bound hCG.

Induction of ovulation in normal rabbits by the administration of 75 IU of hCG can produce 8 to 10 follicles from each ovary which are fertilized and implanted in the uterus after artificial insemination or mating. Two months subsequent to the cessation of immunization, rabbit A, after induction of ovulation by 75 IU of hCG and artificial insemination, showed no sign of ovulation at the time of laparotomy (see FIG. 2). However, the left ovary of rabbit A contained only one large follicle. These observations clearly showed that the anti-receptor antibody in rabbit A suppressed ovarian function and caused a state of infertility. Uteri in both rabbits were normal in size and appearance and there was no evidence of fertilization or implantation, which was further documented by histological section of the uteri of the rabbit. Histological examination of the tissue biopsy did not reveal any pathological or toxic reactions in any of the organs.

Five months after the last immunization, the anti-receptor antibody titer declined to significantly low levels, the anti-receptor antisera also showed binding to $^{125}$ I-hCG. At that time, a repeat induction of ovulation and artificial insemination was followed by another laparotomy in rabbit A (see FIG. 2). The ovaries in rabbit A were found to be of normal size with many follicles, but there was no sign of ovulation or fertilization. Uteri were of normal size and appearance. To rule out the possibility of the endogenous idiotypic antibodies against hCG as the cause of ovulation failure in rabbit A, two weeks later rabbit A was mated and another laparotomy was performed 24 hours later. Both of the ovaries showed many follicles; the right ovary had one antrum follicle and the left ovary had four antrum follicles (see FIG. 2). There was, however, no sign of ovulation indicating that endogenous LH surge in response to mating was also neutralized by endogenous idiotypic anti-antibodies against hCG.

Figure 3:
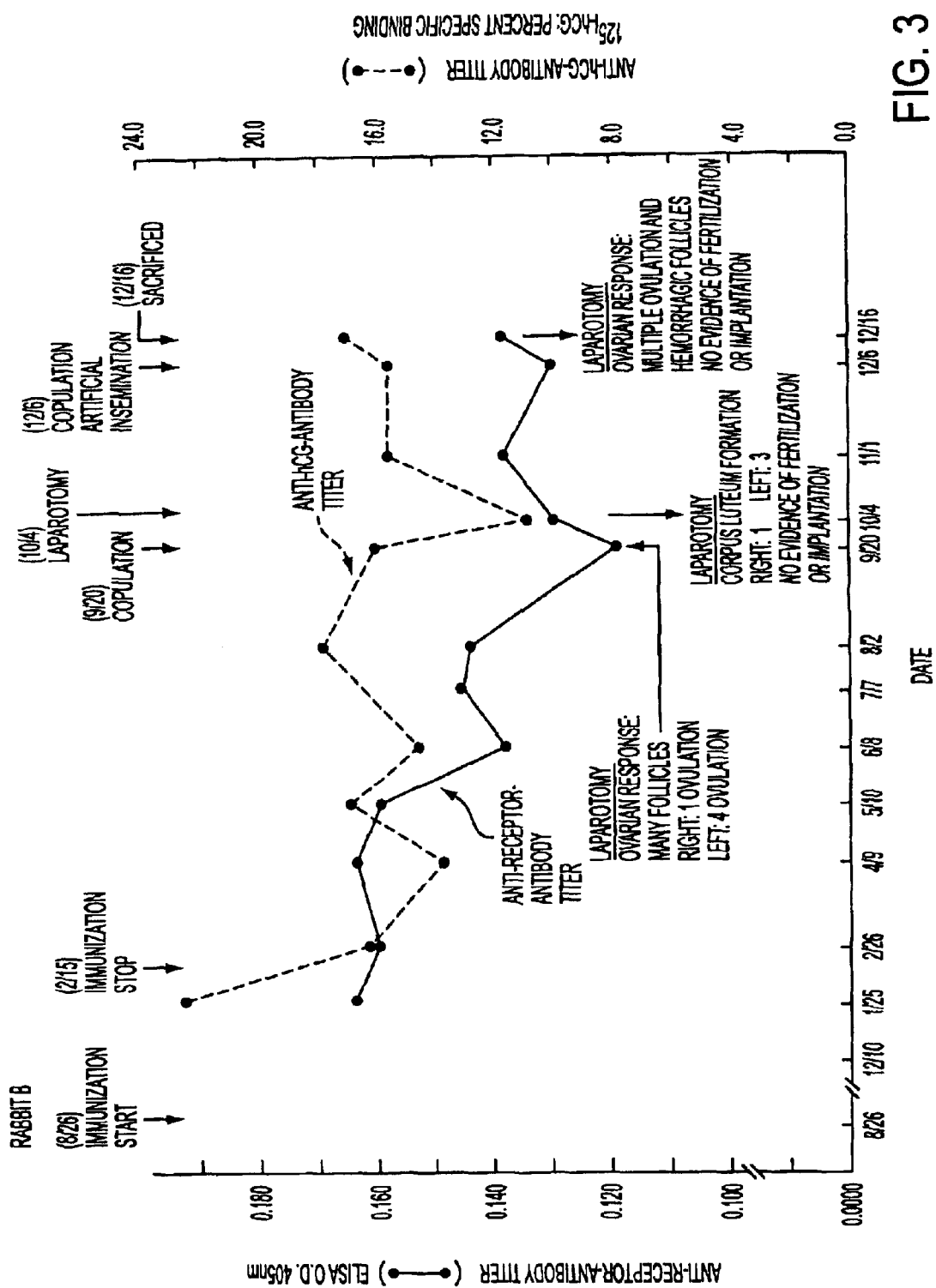

Two weeks later, both rabbits A and B were mated again and 24 hours later laparotomy was performed. In rabbit A there were many follicles but four antrum follicles on the left ovary and one antrum follicle in the right ovary but again there was no ovulation on both ovaries (see FIG. 2). In rabbit B, however, laparotomy revealed four sites of ovulation in the left ovary and one site of ovulation in the right ovary and many antrum follicles but again there was no ovulation on both ovaries (see FIG. 3). Uteri and ovaries appeared normal in rabbit B. Thirteen days later, another laparotomy was performed in rabbit B. As shown in FIG. 3, the left ovary showed three corpora lutea. There was no evidence of fertilization or implantation in any of the rabbits in the presence of the antibody.

Hormonal analysis performed on the sera of rabbits A, B and C prior to immunization and on various days during immunization indicated that the Estradiol levels ranged from 40 to 90 pg/ml in the immunized rabbits, as compared to an average of 80 pg/ml in pooled serum of non-immunized rabbits A, B and C. The LH levels were <2.5 mg/ml and were significantly lower than 14.0 ng/ml of the pooled serum of non-immunized rabbits. The lower levels of LH may be due to its neutralization by idiotypic antibody. The progesterone levels ranged from 0 to 1.6 ng/ml and were also significantly lower than 4.7 ng/ml, of the pooled serum of non-immunized rabbits. The hormonal levels and the reproductive function returned to normal with the disappearance of the antibody from the blood.

The above-described studies demonstrate that active immunization against the receptor provides an effective, safe and reversible interruption of fertility.

EXAMPLE 2

Passive Immunization in Rats

A total of 12 (6 female and 6 male) Sprague-Dawley rats, 55–75 days old were boarded in an animal facility. The female rats were divided into two groups namely an experimental group and a control group. The gamma-globulin fraction was isolated by Rivanol precipitation, as described above, from the serum of rabbits immunized against receptor prepared as described in Reference Example 2 for six months. The gamma-globulin fraction was evaluated in biological as well as in immunological in vitro assays for (1) inhibition of the production of testosterone by rat Leydig cells to the stimulation of hCG, (2) inhibition of specific binding of hCG to membrane receptor of bovine corpora lutea and (3) inhibition of binding of hCG to rat Leydig cells in the presence of the gamma-globulin as described in Example 1 above. Intraperitoneal or intramuscular injections of gamma-globulin were given to the experimental groups of rats. The control group received the same dose of gamma-globulin isolated from normal rat serum. Changes in the estrus cycle were used as an indicator of the specific effect of the passive immunization by gamma-globulin containing receptor antibody. The estrus cycle was evaluated from the vaginal smears obtained twice a day at 9 a.m. and 9 p.m. and examined under a phase contrast microscope by counting the cornified cells, leukocytes and nucleated epithelial cells. The experimental groups showed the antibody titer in the circulation and their estrus cycle was distributed in contrast with a control group. The effects of passive immunization against the receptor antibody demonstrated that disturbances of the estrus cycle of rats occurred and that these disturbances were the result of passive immunization of the rats by the gamma-globulin isolated from receptor rabbit antiserum.

EXAMPLE 3

Active Immunization in Baboons

Figure 4:
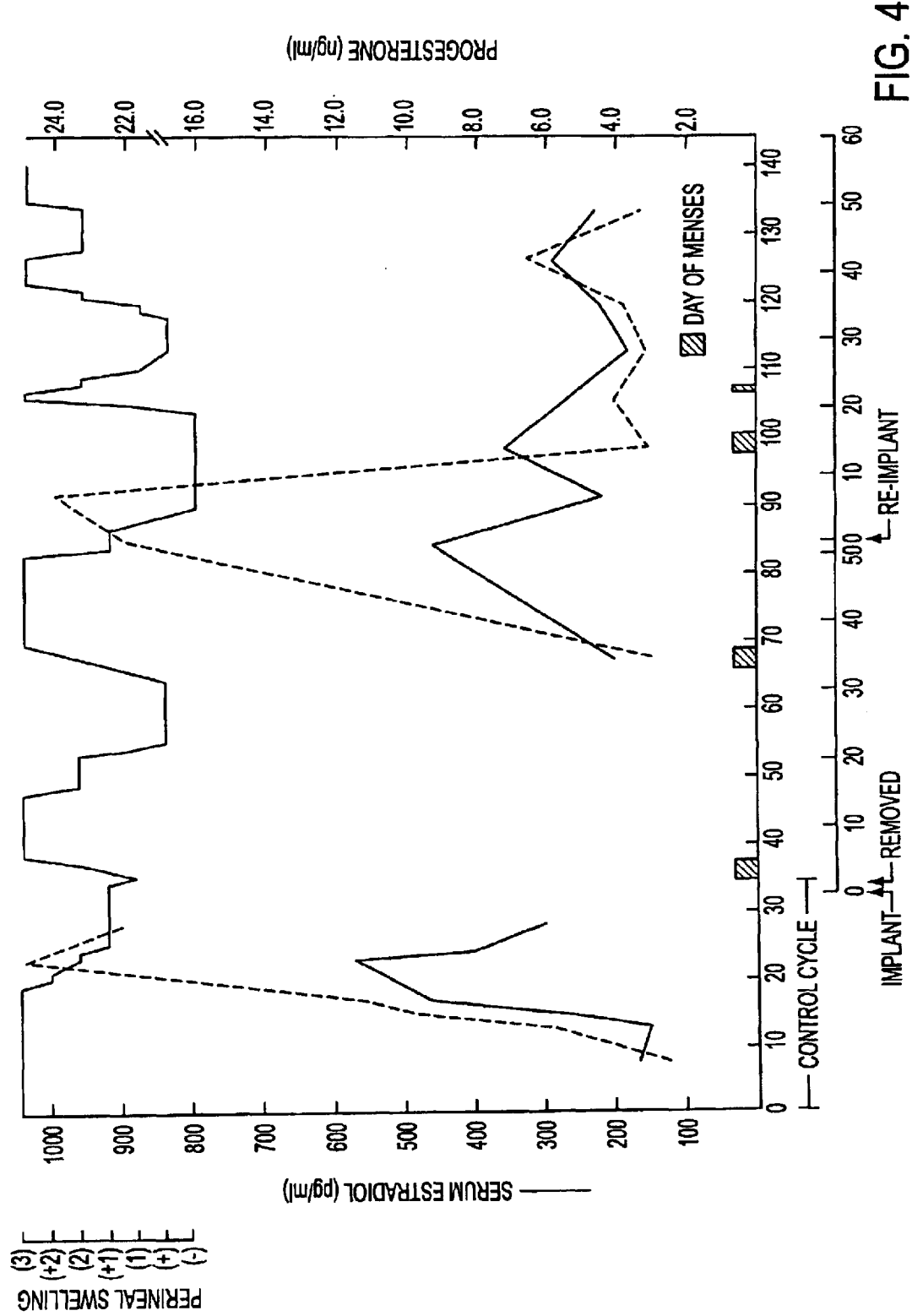
FIGS. 4–6 graphically illustrate the effect of endogenous anti-receptor antibody on reproductive functions in female baboons.
Figure 5:
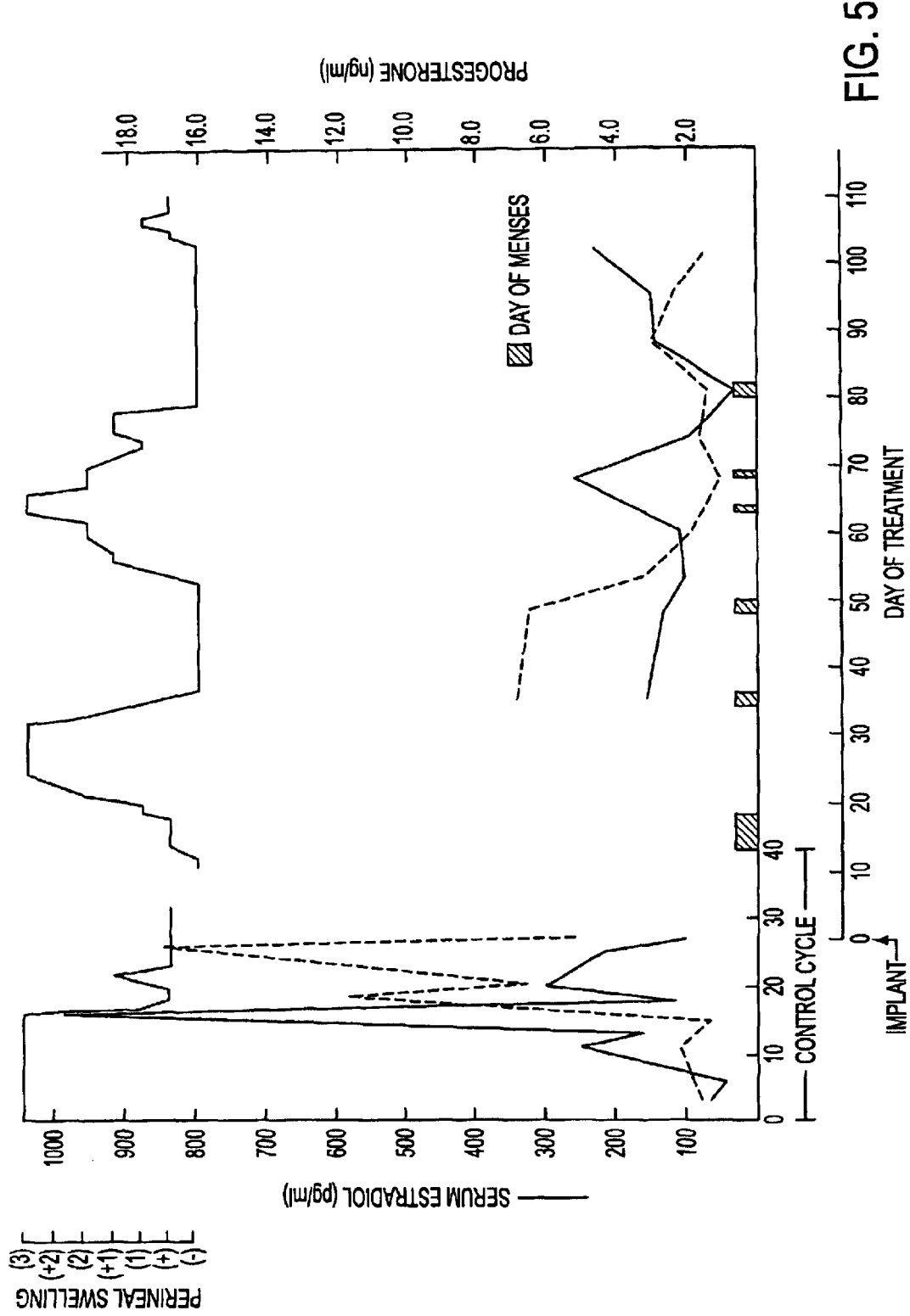
Figure 6:
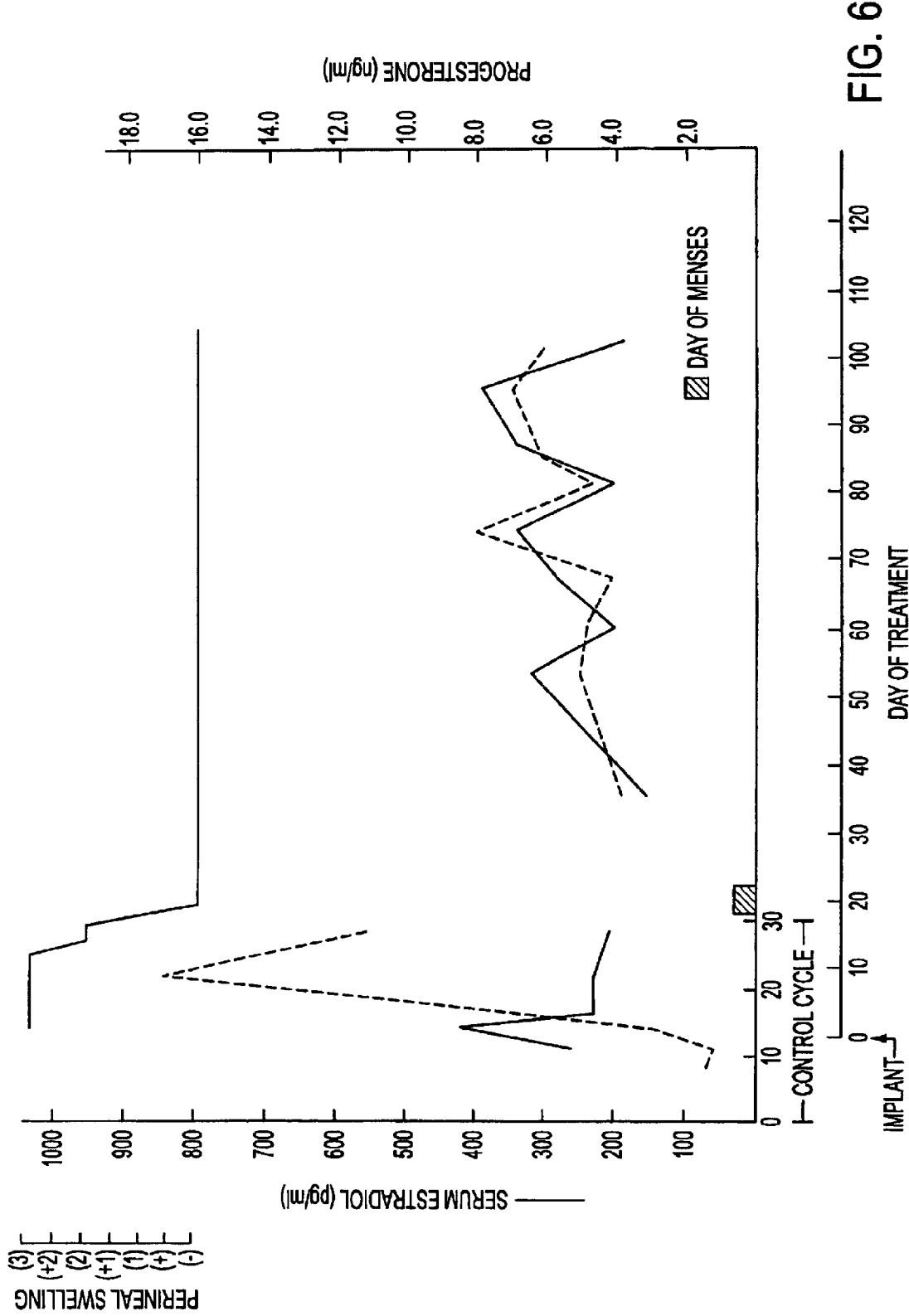

Highly purified LH-hCG receptor was prepared as described in Reference Example 2. Three adult female normally cycling baboons (Papio) were immunized against the receptor using silastic implants prepared as described above. Prior to implantation, the baboons showed normal serum chemistry profile and low density lipoprotein:high density lipoprotein ratio as well as cyclic changes in the serum levels of FSH, LH, $E_2$ and P as determined by radioimmunoassay. Each of the baboons received one implant. Antibody against the receptor was detected in the blood sample at 3–4 weeks after the implantation. One baboon removed the implant and continued to have normal menstrual cycle with cyclic changes in perineal swelling and ovulatory pattern of $E_2$ and P secretion. Hence, the receptor was reimplanted (see FIG. 4). A second baboon, who had been implanted during the luteal phase, had normal menstruation but subsequently had polymenorrhea and partial regression of perineal swelling (see FIG. 5). A third baboon, who had been implanted at midcycle, subsequently showed luteal phase with total regression of perineal swelling and amenorrhea. During the post implant period, there was suppression of midcycle $E_2$ and P surge. The antibody titer rose gradually and reached maximum levels (see FIG. 6). From one of the baboons, who was amenorrheic with no changes in perineal swelling, the implant was removed after approximately 200 days to observe the reversibility of the state of infertility. Two weeks after removal of the implant, when the serum levels of the antibody titers were also in the declining phase, midcycle and luteal phase serum levels of $E_2$ and P rose with typical cyclic changes in the perineal skin, indicative of the ovulatory cycle, and were removed by normal menstrual bleeding. The implants were removed from the other two baboons between 200 and 220 days and these baboons were found to return to fertility. All of the baboons showed no toxic or adverse effects and returned to normal reproductive function and hormonal profile concomitant with the disappearance of the antibody from the blood.

The above-described studies demonstrate that active immunization against the receptor is safe, reversible and a long term contraceptive vaccine.

EXAMPLE 4

Effect of LH-R mab's on the Release of Inositol Trisphosphate ($IP_3$) in Bovine Luteal Cell Cultures To further examine the specificity of LH-R mAb's, bovine luteal cells were pre-labeled, by incubation for three hours with ($^3$H) -inositol (Davis et al., *J. Steroid Biochem.* 32, 643–649, 1987). The cells were washed and preincubated for 30 minutes in Medium 199, containing 0.1% BSA. A 10 mM solution of lithium chloride was added 15 minutes prior to the treatment with LH alone or LH together with LH-R mAb's. After incubation for 30 minutes the reaction was terminated by the addition of 10% trichloroacetic acid. The $^3$H-labeled inositol phosphates were separated by ion exchange chromatography (Davis et al., Biochem. J. 238, 597–604, 1986) and the radioactivity was counted in a scintillation counter, to determine $IP_3$ formation as function of antibody presence in the presence and absence of LH.

Whereas LH and receptor enhanced $IP_3$ formation, addition of a monoclonal antibody to the receptor dampened $IP_3$ formation.

EXAMPLE 5

Bioeffectiveness of LH-R mAb's in Rats In Vivo

Sprague-Dawley, 40 to 45 day old female rats, with normal estrus cycles of 4.5 days, were injected on alternate days intra-peritoneally, with 200 ug protein of mAb in PBS, for six days. Control group was injected with normal rat globulins. Daily vaginal smears of the immunized and control rats were stained with Scherr counterstain and examined under the microscope. Two immunized females were housed with one male per cage and observed for mating and the occurrence of pregnancy.

In passive termination experiments, ten pregnant female mice were injected (i.p.) on alternate days for 12 days with 200 ug of mAb in PBS. Control and injected females were observed for the outcome of pregnancy.

Passive immunization with LH-R mAb's resulted in constant estrus in female rats, up to a period of one month. The rats did not become pregnant when mated. Six weeks after the last injection, the rats returned to normal estrus cycling and become pregnant when exposed to males.

In another experiment with one group of ten pregnant mice, each mouse was injected with mAb to LH-R and a control group of ten pregnant mice received control mouse immunoglobulins. In the control group, eight pregnancies occurred from which 45 live pups were born with an average of 5.62 pups per pregnancy. On the other hand, in the mAb treated group, only three pregnancies occurred, and a total of ten pups at an average of 3.33 per pregnancy were obtained.

In normal male rats, injection of 50 µg and 200 µg of mAb resulted in approximately a 50% reduction in the serum levels of testosterone. There was little change in the histoarchitecture of the testes.

EXAMPLE 6

Effect of LH-R mAb's on Testosterone Production in Rats

Two groups of six Sprague Dawley, 30-day old male rats were injected (s.c.), daily with 50 ug and 100 ug of the mAb's. The mAb's were dissolved in 2.5 ml of PBS. Aliquots of 0.5 ml were injected daily for 5 consecutive days. A group of six rats in the control group were injected with normal globulins. On day six, the animals were sacrificed. Blood was collected by cardiac, puncture for the determination of serum testosterone by radioimmunoassay, and the testes were examined histologically.

LH-R mAb's reduced testosterone output by 25–50%.

EXAMPLE 7

Several of the clones were sequenced. The nucleic acid sequence of portions, and particularly the ends of some of the clones is as follows. Both normal and reverse primers were employed.

Clone 6 1:
CGTAATCATGTCATAGCTGTTTCCTGT-GTGAAATACTCACATTAATTGC GTTGGCCT-CACTGCCCGCTTTCCAGTCGGAAACCT-GTCGTGCCAGCTGC ATTAAGTAATCGGCCAAGGCGCGGG-GAGAGGCGGTTTGCGTATTGGGCG CTCTTTC-CGCTTCCGTCTGCCTCACTGACTCGCT-GCGCTCGGTCGTCCG GCTGCGGCGAGCGTATAGCTACTCAAG(SEQ ID NO:1)

Clone 6 1 Reverse Primer:
TTACCCAACTTAATCCGCCCTTGCAGCA-CATCCCCTTTCGCCAGCTGG TAATAGCGCAA-GAGGCCCCGCACCCGATCGCCCTTCCT-TCAGTTGCGCG CTGAATGGCGAATGGCGTGATGCGG-TATTTTCTCTTAGCATTGTGGTAT TTAA-GATATGGTGATTAGTACAATTGCTCT-GATGCGATAGTTAATAGCG AAGAACATGAGCTGAGGTTG(SEQ ID NO:2)

Reverse of Clone 3 1 Normal Primer:
TCTCCGGCCGTCATGCCGTATTGGTTCG-GATACGGATGTGCTAGGTCCC ACTGCCACG-GCTCCTACTGCTACTCGCGTAA-CAATCTAAAGTATCTGCC ACGGACTGACGCAATCGTTAAAT-TGATACTATTTGATGGCGTAATTTGC AAAG(SEQ ID NO:3)

Clone 3 1:
CTTTGCAAATTACGCCATCAAATAGTAT-CAATTTAACGATTGCGTCAGT CCGTGGCA-GATACCTTTAGATTGTTACGCGAGTAG-CAGTAGGAGCCGTG GCAGTGGGACCTAGCACATCCGTATC-CGAACCAATACGGCATGACGGCC GGAGA(SEQ ID NO:4)

Clone B7a7a10a (hereafter 10a) Normal Primer:
GTAATATGTATAGCTGTTTCCTGTGT-GAAATTGTTATCGCTCACAATTC CACACAAC-TACCCGAGCGCGGAAGCATAAAGTG-TAAAGCCTGGGGTGCC TAATGAGTGAGCTAACTGACACATTAAT(SEQ ID NO:5)

Clone 10a Reverse Primer:
TTGGCACTGGCGTCGTTTAT-CAACGTCGTGACGTGGAAAACGCTGGCTA TCCAACTTAGTCGCTGCAGCACATC-CTAGCTAGTCAGCTGCTAATAGCG Clone 5 3 Reverse Primer:
ATTAACTTTTCTGTCACTTTAATGCTA-GATCCTAGATTACCACCAGTTA GGCCGT-GTCTCTATTTACTTCTGCTTTGC-CTTTCTAAACATTTTTATGA TGAGGATTACATAAAATCGTAAAT-GCGCTTAATACCACTGAATCATACA CTTGAAATGGTAAATTTTTATG-TATTTTTGACCACAATAAAAACTAAAA GCCT (SEQ ID NO:7)

Clone 5 3:
CACGGCCTAACTGGTGGTAATCTAG-GATCTAGCATTAAAGTGACAGAAA AGTTAAT (SEQ ID NO:8)

Clone 4 3R:
AGAGCCCAATACGCAACGCTCTC-CCGCGCGTTGGCCGATTCATTAATGC AGCTG-GCACGACAGGTTCCGACTG-GAAAGCGGGCAGTGAGCGCAACGCA ATTAATGTGAGTTAGCTCACTCATTAGGCACC CCAG(SEQ ID NO:9)

Clone 4 3:
CTGGGGTGCCTAATGAGTGAGCTAACT-CACATTAATTGCGTTGCGCTCA CTGC-CCGCTTTGTCGGAACCTGTCGTCG-CAGCTGCATTAATGAATCGGC CAACGCGCGGGAGAGCGTTGCGTATTGGGC TCT(SEQ ID NO:10)

Reverse of Clone 5 3 Reverse Primer:
AGGCTTTTAGTTTTTATTGTGGT-CAAAAATACATAAAATTTACCATTTC AAGTG-TATGATTCAGTGGTATTAAGCGCATT-TACGATTTTATGTAATCC TCATCATAAAAATGTTTAGAAAGGCAAAGCA GAAGTAAATAGAGA(SEQ ID NO:11)

Reverse of Clone 10a Reverse Primer:
CTCTCGCTATTAGCAGCTGACTAGCTAG-GATGTGCTGCAGCGACTAAGT TGGATAGC-CAGCGTTTTCCACGTCACGACGT-TGATAAACGACGCCAGTG CCAA(SEQ ID NO:12)

EXAMPLE 8

Eight clones of bacteriophage lambda gt11 containing bovine ovarian cDNA inserts were identified by immunoscreening using antibodies to bovine LH-R. The DNA from the clones were extracted, the cDNA inserts were cleaved, subcloned into pUC18 and transformed into JM83 *E. coli*. Recombinant clones were selected on LB-Amp plates containing IPTG-XGAL. The bacteriophage, and in some cases the *E. coli*, then were immunoscreened using five individual monoclonal antibodies to bovine LH-R. The reactivity patterns with the antibodies are as follows.

| Clone | Monoclonal Antibody | | | | |
|---|---|---|---|---|---|
| | 1 | 2 | 3 | 4 | 5 |
| Negative Control | − | − | − | − | − |
| Batch 1, $3_1$ | − | − | − | + | − |
| Clone $2_1$ | − | − | − | − | + |
| Clone $4_3$ | − | − | − | + | − |
| Clone $5_3$ | − | − | − | − | + |
| Clone $6_1$ | − | − | − | + | + |
| B7a7 | − | − | + | − | − |
| B7a5 | − | − | − | + | + |
| B7a2d | − | + | + | + | + |

The first six entries are bacterial colonies and the three B7 entries are bacteriophage.

EXAMPLE 9

The monoclonal antibodies used to screen the clones, such as those disclosed herein, inhibit the action of the hormone on the LH-R. The clones, containing the following cDNA sequences, expressed proteins that bound to the monoclonal antibodies.

Clone $4_3$:
CTCCGCCCAGGGGGCGGCGACGTGC-
GAGCGCTGAGCGAGCTGCAAGGGC GCGCCGT-
GCGGCTGCGTAATCGGCTTTCAAGGT-
GAGCCATT Clone $5_3$:
CGGGTTTTTTTTTTAGGGCTTTT-
TAGTTTTTTTTATTGTGGTTAAAAAA TACAT-
AAAAATTTACCATTTTCAAGTGTATGAT-
TCAGTGGTATTAGCGC
ATTTACGATTTATGTAATCTCATCAT-
AAAATGTTAGAAGGCAAGCGAGT AATGAGAC-
CGCTACTGTGA Clone $6_1$:
CGTAATCATGTCATAGCTGTTTCCTGT-
GTGAAATTGTTATCCGCTCACA ATTCCACA-
CAACATACGAGCCGGAAGCATAAAGTG-
TAAAGCCTGGGGTG
CCTAATGAGTGAGCTAACTCACATTAAT-
TGCGTTGCGCTCACTGCCCGC TTTCCAGTCGG-
GAAACCTGTCGTGCCAGCTGCATTAAT-
GAATCGGCCAA
CGCGCGGGGAGAGGCGGTTTGCGTAT-
TGGGCGCTCTTTCCGCTTCCGTC TGCCTCACT-
GACTCGCTGCGCTCGGTCGTCCGGCT-
GCGGCGAGCGTATA GCTACTCAAG While the instant invention has been described in detail and with reference to specific embodiments thereof, it will be apparent to one skilled in the art that various changes and modifications could be made therein without departing from the spirit and scope thereof.

All references cited herein are herein incorporated by reference.

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 223 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CGTAATCATG TCATAGCTGT TTCCTGTGTG AAATACTCAC ATTAATTGCG TTGGCCTCAC      60

TGCCCGCTTT CCAGTCGGAA ACCTGTCGTG CCAGCTGCAT TAAGTAATCG GCCAAGGCGC     120

GGGGAGAGGC GGTTTGCGTA TTGGGCGCTC TTTCCGCTTC CGTCTGCCTC ACTGACTCGC     180

TGCGCTCGGT CGTCCGGCTG CGGCGAGCGT ATAGCTACTC AAG                      223
```

(2) INFORMATION FOR SEQ ID NO:2:

(i) SEQUENCE CHARACTERISTICS:
      (A) LENGTH: 216 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
TTACCCAACT TAATCCGCCC TTGCAGCACA TCCCCCTTTC GCCAGCTGGT AATAGCGCAA         60

GAGGCCCCGC ACCCGATCGC CCTTCCTTCA GTTGCGCGCT GAATGGCGAA TGGCGTGATG        120

CGGTATTTTC TCTTAGCATT GTGGTATTTA AGATATGGTG ATTAGTACAA TTGCTCTGAT        180

GCGATAGTTA ATAGCGAAGA ACATGAGCTG AGGTTG                                  216
```

(2) INFORMATION FOR SEQ ID NO:3:

(i) SEQUENCE CHARACTERISTICS:
        (A) LENGTH: 151 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
TCTCCGGCCG TCATGCCGTA TTGGTTCGGA TACGGATGTG CTAGGTCCCA CTGCCACGGC         60

TCCTACTGCT ACTCGCGTAA CAATCTAAAG TATCTGCCAC GGACTGACGC AATCGTTAAA        120

TTGATACTAT TTGATGGCGT AATTTGCAAA G                                       151
```

(2) INFORMATION FOR SEQ ID NO:4:

(i) SEQUENCE CHARACTERISTICS:
        (A) LENGTH: 152 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
CTTTGCAAAT TACGCCATCA AATAGTATCA ATTTAACGAT TGCGTCAGTC CGTGGCAGAT         60

ACCTTTAGAT TGTTACGCGA GTAGCAGTAG GAGCCGTGGC AGTGGGACCT AGCACATCCG        120

TATCCGAACC AATACGGCAT GACGGCCGGA GA                                      152
```

(2) INFORMATION FOR SEQ ID NO:5:

(i) SEQUENCE CHARACTERISTICS:
        (A) LENGTH: 126 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
GTAATATGTA TAGCTGTTTC CTGTGTGAAA TTGTTATCGC TCACAATTCC ACACAACTAC         60

CCGAGCGCGG AAGCATAAAG TGTAAAGCCT GGGGTGCCTA ATGAGTGAGC TAACTGACAC        120

ATTAAT                                                                   126
```

(2) INFORMATION FOR SEQ ID NO:6:

(i) SEQUENCE CHARACTERISTICS:
        (A) LENGTH: 102 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTGGCACTGG CGTCGTTTAT CAACGTCGTG ACGTGGAAAA CGCTGGCTAT CCAACTTAGT         60
```

CGCTGCAGCA CATCCTAGCT AGTCAGCTGC TAATAGCGAG AG                102

(2) INFORMATION FOR SEQ ID NO:7:

(i) SEQUENCE CHARACTERISTICS:
        (A) LENGTH: 200 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

ATTAACTTTT CTGTCACTTT AATGCTAGAT CCTAGATTAC CACCAGTTAG GCCGTGTCTC     60

TATTTACTTC TGCTTTGCCT TTCTAAACAT TTTTATGATG AGGATTACAT AAAATCGTAA    120

ATGCGCTTAA TACCACTGAA TCATACACTT GAAATGGTAA ATTTTTATGT ATTTTTGACC    180

ACAATAAAAA CTAAAAGCCT                                                200

(2) INFORMATION FOR SEQ ID NO:8:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CACGGCCTAA CTGGTGGTAA TCTAGGATCT AGCATTAAAG TGACAGAAAA GTTAAT         56

(2) INFORMATION FOR SEQ ID NO:9:

(i) SEQUENCE CHARACTERISTICS:
        (A) LENGTH: 134 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

AGAGCCCAAT ACGCAACGCT CTCCCGCGCG TTGGCCGATT CATTAATGCA GCTGGCACGA     60

CAGGTTCCGA CTGGAAAGCG GGCAGTGAGC GCAACGCAAT TAATGTGAGT TAGCTCACTC    120

ATTAGGCACC CCAG                                                      134

(2) INFORMATION FOR SEQ ID NO:10:

(i) SEQUENCE CHARACTERISTICS:
        (A) LENGTH: 131 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTGGGGTGCC TAATGAGTGA GCTAACTCAC ATTAATTGCG TTGCGCTCAC TGCCCGCTTT     60

GTCGGAACCT GTCGTCGCAG CTGCATTAAT GAATCGGCCA ACGCGCGGGA GAGCGTTGCG    120

TATTGGGCTC T                                                         131

(2) INFORMATION FOR SEQ ID NO:11:

(i) SEQUENCE CHARACTERISTICS:
    (A) LENGTH: 143 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:11:

```
AGGCTTTTAG TTTTTATTGT GGTCAAAAAT ACATAAAATT TACCATTTCA AGTGTATGAT      60

TCAGTGGTAT TAAGCGCATT TACGATTTTA TGTAATCCTC ATCATAAAAA TGTTTAGAAA     120

GGCAAAGCAG AAGTAAATAG AGA                                             143
```

(2) INFORMATION FOR SEQ ID NO:12:

(i) SEQUENCE CHARACTERISTICS:
      (A) LENGTH: 102 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:12:

```
CTCTCGCTAT TAGCAGCTGA CTAGCTAGGA TGTGCTGCAG CGACTAAGTT GGATAGCCAG      60

CGTTTTCCAC GTCACGACGT TGATAAACGA CGCCAGTGCC AA                        102
```

(2) INFORMATION FOR SEQ ID NO:13:

(i) SEQUENCE CHARACTERISTICS:
      (A) LENGTH: 90 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:13:

```
CTCCGCCCAG GGGGCGGCGA CGTGCGAGCG CTGAGCGAGC TGCAAGGGCG CGCCGTGCGG      60

CTGCGTAATC GGCTTTCAAG GTGAGCCATT                                       90
```

(2) INFORMATION FOR SEQ ID NO:14:

(i) SEQUENCE CHARACTERISTICS:
      (A) LENGTH: 166 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:14:

```
CGGGTTTTTT TTTTAGGGCT TTTTAGTTTT TTTTATTGTG GTTAAAAAAT ACATAAAAAT      60

TTACCATTTT CAAGTGTATG ATTCAGTGGT ATTAGCGCAT TTACGATTTA TGTAATCTCA     120

TCATAAAATG TTAGAAGGCA AGCGAGTAAT GAGACCGCTA CTGTGA                    166
```

(2) INFORMATION FOR SEQ ID NO:15:

(i) SEQUENCE CHARACTERISTICS:
      (A) LENGTH: 304 base pairs
      (B) TYPE: nucleic acid
      (C) STRANDEDNESS: single
      (D) TOPOLOGY: linear -continued (ii) MOLECULE TYPE: DNA (genomic)

(xi) SEQUENCE DESCRIPTION: SEQ ID NO:15:

| | | | | | | |
|---|---|---|---|---|---|---|
| CGTAATCATG | TCATAGCTGT | TTCCTGTGTG | AAATTGTTAT | CCGCTCACAA | TTCCACACAA | 60 |
| CATACGAGCC | GGAAGCATAA | AGTGTAAAGC | CTGGGGTGCC | TAATGAGTGA | GCTAACTCAC | 120 |
| ATTAATTGCG | TTGCGCTCAC | TGCCCGCTTT | CCAGTCGGGA | AACCTGTCGT | GCCAGCTGCA | 180 |
| TTAATGAATC | GGCCAACGCG | CGGGGAGAGG | CGGTTTGCGT | ATTGGGCGCT | CTTTCCGCTT | 240 |
| CCGTCTGCCT | CACTGACTCG | CTGCGCTCGG | TCGTCCGGCT | GCGGCGAGCG | TATAGCTACT | 300 |
| CAAG | | | | | | 304 |

What is claimed is:

1. An isolated nucleic acid molecule that encodes a polypeptide, wherein said polypeptide is a fragment of the bovine luteinizing hormone/chorionic gonadotropin receptor, and wherein said molecule consists of the nucleotide sequence of SEQ ID NO: 8.

2. A recombinant vector comprising the nucleic acid of claim 1.

* * * * *

UNITED STATES PATENT AND TRADEMARK OFFICE
CERTIFICATE OF CORRECTION

PATENT NO.   : 6,723,556 B1
DATED        : April 20, 2004
INVENTOR(S)  : Saxena, Brij B. et al.

It is certified that error appears in the above-identified patent and that said Letters Patent is hereby corrected as shown below:

Column 1,
Line 22, just before "FIELD OF THE INVENTION" please add the following:

-- This invention was made with Government support from the National Institutes of Health (NIH) under Grant No. HD20546. The Government has certain rights in the invention --.

Signed and Sealed this

Fifth Day of October, 2004

JON W. DUDAS
*Director of the United States Patent and Trademark Office*